(12) United States Patent
Prokop et al.

(10) Patent No.: US 7,632,666 B2
(45) Date of Patent: Dec. 15, 2009

(54) METHOD OF PRODUCTION OF OPTICALLY ACTIVE HALOHYDROCARBONS AND ALCOHOLS USING HYDROLYTIC DEHALOGENATION CATALYSED BY HALOALKANE DEHALOGENASES

(75) Inventors: Zbynek Prokop, Brno (CZ); Jiri Damborsky, Brno (CZ); Dick B. Janssen, Roden (NL); Yuji Nagata, Sendai (JP)

(73) Assignee: Masarykova Univerzita V Brne, Brno (CZ)

( * ) Notice: Subject to any disclaimer, the term of this patent is extended or adjusted under 35 U.S.C. 154(b) by 0 days.

(21) Appl. No.: 11/844,463

(22) Filed: Aug. 24, 2007

(65) Prior Publication Data

US 2008/0102501 A1 May 1, 2008

Related U.S. Application Data

(63) Continuation-in-part of application No. 11/793,635, filed on Jun. 20, 2007.

(30) Foreign Application Priority Data

Dec. 23, 2005 (WO) ............... PCT/CZ2005/000099

(51) Int. Cl.
*C12P 7/02* (2006.01)
*C12P 5/00* (2006.01)
*C12N 9/00* (2006.01)
*C12N 9/14* (2006.01)

(52) U.S. Cl. ........................ 435/166; 435/155; 435/183; 435/195

(58) Field of Classification Search .................. None
See application file for complete search history.

(56) References Cited

FOREIGN PATENT DOCUMENTS

| WO | WO 02/068583 | * | 9/2002 |
| WO | WO2006079295 | * | 8/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kaneko et al. Accession P59337, Feb. 22, 2003.*

* cited by examiner

*Primary Examiner*—Christian L Fronda
(74) *Attorney, Agent, or Firm*—Notaro & Michalos P.C.

(57) ABSTRACT

A method of production of optically active compounds, particularly halohydrocarbons, haloalcohols, alcohols, halopolyols and polyols using hydrolytic dehalogenation of racemic or prochiral halegenhydrocarbons by dehalohenation catalysed by haloalkane dehalogenases (the enzyme code number EC 3.8.1.5) where at least one wild type or modified haloalkane dehalogenase is applied to at least one racemic or prochiral chlorinated, brominated or iodinated compound at the temperature ranged between +10 and +70° C. and pH value between 4.0 and 12.0, in aqueous system or in a monophasic organic solution or in a monophasic organic/aqueous solution or in organic/aqueous biphasic systems.

5 Claims, 2 Drawing Sheets

SEQUENCE LISTING

<160> NUMBER OF SEQ ID NOS: 20

<210> SEQ ID NO 1
<211> LENGTH: 933
<212> TYPE: DNA
<213> ORGANISM: Bradyrhizobium japonicum

<400> SEQUENCE: 1

```
atgagcaagc caatcgagat cgagattcgc agagcgcccg tgctgggaag cagcatggct      60
taccgcgaga cgggtgcgca ggatgcgccg gtcgtgctgt tcctgcacgg caacccgacc     120
tcgtcgcaca tctggcgcaa catcctgccg ttggtgtcac cggtcgcgca ttgcattgcg     180
cccgatctca tcggcttcgg ccaatccggt aagcctgaca tcgcctaccg cttcttcgac     240
catgtccgct atctcgatgc gttcatcgaa cagcgcggcg tcacatcggc ctatctcgtc     300
gcgcaggact ggggcacggc gctcgcattt catctcgccg cgcgccggcc ggatttcgta     360
cgcggattag ccttcatgga attcatccgc ccgatgccga cctggcagga tttccaccat     420
accgaggtcg cggaggagca agatcatgcc gaggcggcga gggcggtctt cgcaagttc      480
aggacgccgg gcgagggtga ggccatgatc ctcgaggcga atgcgttcgt cgagcgcgtt     540
ctgcccggcg gaatcgtccg caagctcggc gacgaagaaa tggcgcccta tcgcacgccg     600
ttcccgacgc ccgagagtcg ccgccccgtt cttgcgtttc cccgcgagct gccgatcgca     660
ggtgagcctg ccgatgtcta tgaggcgctc aatccgccc atgcggcgct ggccgcatct      720
tcctatccga aactgctgtt cacgggcgaa ccgggcgcgc tcgtctcgcc ggaatttgcc     780
gagcggtttg cggcctcgct gacgcgttgc gcgttgatcc ggctcggcgc gggattgcac     840
tatctgcagg aggaccacgc tgacgcaatc ggccgatcgg tggccggctg gatcgccggc     900
atcgaagcgg tgcgtccgca gctcgccgcg tga                                  933
```

<210> SEQ ID NO 2
<211> LENGTH: 310
<212> TYPE: PRT
<213> ORGANISM: Bradyrhizobium japonicum

<400> SEQUENCE: 2

```
Met Ser Lys Pro Ile Glu Ile Glu Ile Arg Arg Ala Pro Val Leu Gly
  1               5                  10                  15

Ser Ser Met Ala Tyr Arg Glu Thr Gly Ala Gln Asp Ala Pro Val Val
             20                  25                  30

Leu Phe Leu His Gly Asn Pro Thr Ser Ser His Ile Trp Arg Asn Ile
         35                  40                  45

Leu Pro Leu Val Ser Pro Val Ala His Cys Ile Ala Pro Asp Leu Ile
     50                  55                  60

Gly Phe Gly Gln Ser Gly Lys Pro Asp Ile Ala Tyr Arg Phe Phe Asp
 65                  70                  75                  80

His Val Arg Tyr Leu Asp Ala Phe Ile Glu Gln Arg Gly Val Thr Ser
                 85                  90                  95

Ala Tyr Leu Val Ala Gln Asp Trp Gly Thr Ala Leu Ala Phe His Leu
            100                 105                 110

Ala Ala Arg Arg Pro Asp Phe Val Arg Gly Leu Ala Phe Met Glu Phe
        115                 120                 125

Ile Arg Pro Met Pro Thr Trp Gln Asp Phe His His Thr Glu Val Ala
    130                 135                 140
```

-continued

```
Glu Gln Asp His Ala Glu Ala Ala Arg Ala Val Phe Arg Lys Phe
145                 150                 155                 160

Arg Thr Pro Gly Glu Gly Ala Met Ile Leu Glu Ala Asn Ala Phe
            165                 170                 175

Val Glu Arg Val Leu Pro Gly Gly Ile Val Arg Lys Leu Gly Asp Glu
        180                 185                 190

Glu Met Ala Pro Tyr Arg Thr Pro Phe Pro Thr Pro Glu Ser Arg Arg
        195                 200                 205

Pro Val Leu Ala Phe Pro Arg Glu Leu Pro Ile Ala Gly Glu Pro Ala
        210                 215                 220

Asp Val Tyr Glu Ala Leu Gln Ser Ala His Ala Ala Leu Ala Ala Ser
225                 230                 235                 240

Ser Tyr Pro Lys Leu Leu Phe Thr Gly Glu Pro Gly Ala Leu Val Ser
                245                 250                 255

Pro Glu Phe Ala Glu Arg Phe Ala Ala Ser Leu Thr Arg Cys Ala Leu
            260                 265                 270

Ile Arg Leu Gly Ala Gly Leu His Tyr Leu Gln Glu Asp His Ala Asp
        275                 280                 285

Ala Ile Gly Arg Ser Val Ala Gly Trp Ile Ala Gly Ile Glu Ala Val
        290                 295                 300

Arg Pro Gln Leu Ala Ala
305                 310
```

<210> SEQ ID NO 3
<211> LENGTH: 891
<212> TYPE: DNA
<213> ORGANISM: Sphingomonas paucimobilis

<400> SEQUENCE: 3

```
atgagcctcg gcgcaaagcc atttggcgag aagaaattca ttgagatcaa gggccggcgc    60
atggcctata tcgatgaagg gaccggcgat ccgatcctct ccagcacgg caatccgacg     120
tcgtcctatc tgtggcgcaa tatcatgccg cattgcgccg gctgggacg gctgatcgcc     180
tgtgacctga tcggcatggg cgattcggac aagctcgatc cgtcggggcc cgagcgttat    240
gcctatgccg agcatcgtga ctatctcgac gcgctgtggg aggcgctcga tctcggggac    300
agggttgttc tggtcgtgca tgactggggg tccgccctcg gcttcgactg gcccgccgc    360
caccgcgagc gtgtacaggg gattgcctat atggaagcga tcgccatgcc gatcgaatgg    420
gcggattttc ccgaacagga tcgcgatctg tttcaggcct ttcgctcgca ggcgggcgaa    480
gaattggtgt tgcaggacaa tgttttttgtc gaacaagttc tccccggatt gatcctgcgc    540
cccttaagcg aagcggagat ggccgccta tcgcgagccct tcctcgccgc cggcgaagcc   600
cgtcgaccga ccctgtcttg gcctcgccaa atcccgatcg caggcacccc ggccgacgtg    660
gtcgcgatcg cccgggacta tgccggctgg ctcagcgaaa gccgattcc gaaactcttc    720
atcaacgccg agccgggagc cctgaccacg ggccgaatgc gcgacttctg ccgcacatgg    780
ccaaaccaga ccgaaatcac ggtcgcaggc gcccatttca tccaggagga cagtccggac    840
gagattggcg cggcgattgc ggcgtttgtc cggcgattgc gcccagcata a            891
```

<210> SEQ ID NO 4
<211> LENGTH: 296
<212> TYPE: PRT
<213> ORGANISM: Sphingomonas paucimobilis

<400> SEQUENCE: 4

```
Met Ser Leu Gly Ala Lys Pro Phe Gly Glu Lys Lys Phe Ile Glu Ile
1               5                   10                  15

Lys Gly Arg Arg Met Ala Tyr Ile Asp Glu Gly Thr Gly Asp Pro Ile
            20                  25                  30

Leu Phe Gln His Gly Asn Pro Thr Ser Ser Tyr Leu Trp Arg Asn Ile
        35                  40                  45

Met Pro His Cys Ala Gly Leu Gly Arg Leu Ile Ala Cys Asp Leu Ile
    50                  55                  60

Gly Met Gly Asp Ser Asp Lys Leu Asp Pro Ser Gly Pro Glu Arg Tyr
65                  70                  75                  80

Ala Tyr Ala Glu His Arg Asp Tyr Leu Asp Ala Leu Trp Glu Ala Leu
                85                  90                  95

Asp Leu Gly Asp Arg Val Val Leu Val Val His Asp Trp Gly Ser Ala
            100                 105                 110

Leu Gly Phe Asp Trp Ala Arg Arg His Arg Glu Arg Val Gln Gly Ile
        115                 120                 125

Ala Tyr Met Glu Ala Ile Ala Met Pro Ile Glu Trp Ala Asp Phe Pro
    130                 135                 140

Glu Gln Asp Arg Asp Leu Phe Gln Ala Phe Arg Ser Gln Ala Gly Glu
145                 150                 155                 160

Glu Leu Val Leu Gln Asp Asn Val Phe Val Glu Gln Val Leu Pro Gly
            165                 170                 175

Leu Ile Leu Arg Pro Leu Ser Glu Ala Glu Met Ala Ala Tyr Arg Glu
        180                 185                 190

Pro Phe Leu Ala Ala Gly Glu Ala Arg Arg Pro Thr Leu Ser Trp Pro
    195                 200                 205

Arg Gln Ile Pro Ile Ala Gly Thr Pro Ala Asp Val Val Ala Ile Ala
210                 215                 220

Arg Asp Tyr Ala Gly Trp Leu Ser Glu Ser Pro Ile Pro Lys Leu Phe
225                 230                 235                 240

Ile Asn Ala Glu Pro Gly Ala Leu Thr Thr Gly Arg Met Arg Asp Phe
            245                 250                 255

Cys Arg Thr Trp Pro Asn Gln Thr Glu Ile Thr Val Ala Gly Ala His
        260                 265                 270

Phe Ile Gln Glu Asp Ser Pro Asp Glu Ile Gly Ala Ala Ile Ala Ala
    275                 280                 285

Phe Val Arg Arg Leu Arg Pro Ala
    290                 295

<210> SEQ ID NO 5
<211> LENGTH: 882
<212> TYPE: DNA
<213> ORGANISM: Rhodococcus rhodochrous

<400> SEQUENCE: 5
atgtcagaaa tcggtacagg cttccccttc gaccccatt  atgtggaagt cctgggcgag      60
cgtatgcact acgtcgatgt tggaccgcgg gatggcacgc ctgtgctgtt cctgcacggt     120
aacccgacct cgtcctacct gtggcgcaac atcatcccgc atgtagcacc gagtcatcgg     180
tgcattgctc cagacctgat cgggatggga aaatcggaca accagacct cgattatttc     240 ttcgacgacc acgtccgcta cctcgatgcc ttcatcgaag ccttgggttt ggaagaggtc     300
gtcctggtca tccacgactg ggctcagct ctcggattcc actgggccaa gcgcaatccg     360
gaacgggtca aggtattgc atgtatggaa ttcatccggc ctatcccgac gtgggacgaa     420
```

```
tggccggaat tcgcccgtga gaccttccag gccttccgga ccgccgacgt cggccgagag      480
ttgatcatcg atcagaacgc tttcatcgag ggtgcgctcc cgaaatgcgt cgtccgtccg      540
cttacggagg tcgagatgga ccactatcgc gagcccttcc tcaagcctgt tgaccgagag      600
ccactgtggc gattccccaa cgagctgccc atcgccggtg agcccgcgaa catcgtcgcg      660
ctcgtcgagg catacatgaa ctggctgcac cagtcacctg tcccgaagtt gttgttctgg      720
ggcacacccg gcgtactgat ccccccggcc gaagccgcga gacttgccga aagcctcccc      780
aactgcaaga cagtggacat cggcccggga ttgcactacc tccaggaaga caacccggac      840
cttatcggca gtgagatcgc gcgctggctc cccgcactct ag                        882
```

```
<210> SEQ ID NO 6
<211> LENGTH: 293
<212> TYPE: PRT
<213> ORGANISM: Rhodococcus rhodochrous

<400> SEQUENCE: 6

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Cys
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Lys Cys
                165                 170                 175

Val Val Arg Pro Leu Thr Glu Val Glu Met Asp His Tyr Arg Glu Pro
                180                 185                 190

Phe Leu Lys Pro Val Asp Arg Glu Pro Leu Trp Arg Phe Pro Asn Glu
            195                 200                 205

Leu Pro Ile Ala Gly Glu Pro Ala Asn Ile Val Ala Leu Val Glu Ala
        210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu His
                260                 265                 270

Tyr Leu Gln Glu Asp Asn Pro Asp Leu Ile Gly Ser Glu Ile Ala Arg
            275                 280                 285

Trp Leu Pro Ala Leu
```

<210> SEQ ID NO 7
<211> LENGTH: 903
<212> TYPE: DNA
<213> ORGANISM: Mycobacterium bovis

<400> SEQUENCE: 7

| | | | | | |
|---|---|---|---|---|---|
| atgacagcat | tcggcgtcga | gccctacggg | cagccgaagt | acctagaaat | cgccgggaag | 60 |
| cgcatggcgt | atatcgacga | aggcaagggt | gacgccatcg | tctttcagca | cggcaacccc | 120 |
| acgtcgtctt | acttgtggcg | caacatcatg | ccgcacttgg | aagggctggg | ccggctggtg | 180 |
| gcctgcgatc | tgatcgggat | gggcgcgtcg | gacaagctca | gcccatcggg | acccgaccgc | 240 |
| tatagctatg | gcgagcaacg | agactttttg | ttcgcgctct | gggatgcgct | cgacctcggc | 300 |
| gaccacgtgg | tactggtgct | gcacgactgg | ggctcggcgc | tcggcttcga | ctgggctaac | 360 |
| cagcatcgcg | accgagtgca | ggggatcgcg | ttcatggaag | cgatcgtcac | cccgatgacg | 420 |
| tgggcggact | ggccgccggc | cgtgcggggt | gtgttccagg | gtttccgatc | gcctcaaggc | 480 |
| gagccaatgg | cgttggagca | aacatctttt | gtcgaacggg | tgctgcccgg | ggcgatcctg | 540 |
| cgacagctca | gcgacgagga | aatgaaccac | tatcggcggc | cattcgtgaa | cggcggcgag | 600 |
| gaccgtcgcc | ccacgttgtc | gtggccacga | aaccttccaa | tcgacggtga | gcccgccgag | 660 |
| gtcgtcgcgt | tggtcaacga | gtaccggagc | tggctcgagg | aaaccgacat | gccgaaactg | 720 |
| ttcatcaacg | cccgagcccgg | cgcgatcatc | accggccgca | tccgtgacta | tgtcaggagc | 780 |
| tggcccaacc | agaccgaaat | cacagtgccc | ggcgtgcatt | tcgttcagga | ggacagccca | 840 |
| gaggaaatcg | gtgcggccat | agcacagttc | gtccggcagc | tccggtcggc | ggccggcgtc | 900 |
| tga | | | | | | 903 |

<210> SEQ ID NO 8
<211> LENGTH: 300
<212> TYPE: PRT
<213> ORGANISM: Mycobacterium bovis

<400> SEQUENCE: 8

Met Thr Ala Phe Gly Val Glu Pro Tyr Gly Gln Pro Lys Tyr Leu Glu
1               5                   10                  15

Ile Ala Gly Lys Arg Met Ala Tyr Ile Asp Glu Gly Lys Gly Asp Ala
            20                  25                  30

Ile Val Phe Gln His Gly Asn Pro Thr Ser Ser Tyr Leu Trp Arg Asn
        35                  40                  45

Ile Met Pro His Leu Glu Gly Leu Gly Arg Leu Val Ala Cys Asp Leu
    50                  55                  60

Ile Gly Met Gly Ala Ser Asp Lys Leu Ser Pro Ser Gly Pro Asp Arg
65                  70                  75                  80

Tyr Ser Tyr Gly Glu Gln Arg Asp Phe Leu Phe Ala Leu Trp Asp Ala
                85                  90                  95

Leu Asp Leu Gly Asp His Val Val Leu Val Leu His Asp Trp Gly Ser
            100                 105                 110

Ala Leu Gly Phe Asp Trp Ala Asn Gln His Arg Asp Arg Val Gln Gly
        115                 120                 125

Ile Ala Phe Met Glu Ala Ile Val Thr Pro Met Thr Trp Ala Asp Trp
    130                 135                 140

Pro Pro Ala Val Arg Gly Val Phe Gln Gly Phe Arg Ser Pro Gln Gly
145                 150                 155                 160

```
Glu Pro Met Ala Leu Glu His Asn Ile Phe Val Glu Arg Val Leu Pro
            165                 170                 175
Gly Ala Ile Leu Arg Gln Leu Ser Asp Glu Glu Met Asn His Tyr Arg
            180                 185                 190
Arg Pro Phe Val Asn Gly Gly Glu Asp Arg Arg Pro Thr Leu Ser Trp
        195                 200                 205
Pro Arg Asn Leu Pro Ile Asp Gly Glu Pro Ala Glu Val Val Ala Leu
        210                 215                 220
Val Asn Glu Tyr Arg Ser Trp Leu Glu Glu Thr Asp Met Pro Lys Leu
225                 230                 235                 240
Phe Ile Asn Ala Glu Pro Gly Ala Ile Ile Thr Gly Arg Ile Arg Asp
                245                 250                 255
Tyr Val Arg Ser Trp Pro Asn Gln Thr Glu Ile Thr Val Pro Gly Val
            260                 265                 270
His Phe Val Gln Glu Asp Ser Pro Glu Glu Ile Gly Ala Ala Ile Ala
        275                 280                 285
Gln Phe Val Arg Gln Leu Arg Ser Ala Ala Gly Val
        290                 295                 300

<210> SEQ ID NO 9
<211> LENGTH: 903
<212> TYPE: DNA
<213> ORGANISM: Mycobacterium bovis

<400> SEQUENCE: 9
atggatgtcc tacgcacccc agactcccgg ttcgaacacc tggtgggcta cccgtttgca      60
ccgcactatg tcgatgtgac ggccggcgac acccagccgt tgcgaatgca ctacgtcgac     120
gagggcccgg gcgacggtcc gccgatcgtc ttgctgcacg gcgagcccac ctggagttat     180
ctgtaccgaa ccatgattcc gccgctctcc gccgccgggc accgtgtgct cgcgcccgac     240
ctgatcggct tcggccgctc cgacaagccg actcgcatcg aggactacac ctacctgcgg     300
cacgtcgagt gggtgacgtc ctggttcgag aatctcgacc tgcacgacgt acgctcttc      360
gtgcaggact gggggtcatt gatcggtctg cgcatcgctg ccgagcacgg tgaccggatc     420
gcgcggctgg tggtcgccaa cgggtttctc cccgccgcgc aggggcgcac ccactcccc      480
ttctacgtgt ggcgggcgtt tgcgcgctat tctccggtgc ttcccgctgg ccgtctggtg     540
aacttcggca ccgtccacag ggttcccgcc ggggtccgag ccggctacga tgcaccttc      600
cccgacaaaa cgtatcaagc cggcgcccgg cgttcccac ggttggtgcc gacctcaccc      660
gacgatccgg cggtaccggc caaccgcgcg gcatgggaag ccctgggccg gtgggacaaa     720
ccgttccttg ccatcttcgg ttatcgcgac ccgatactcg gcaagcggac ggtccgctg      780
atcaagcaca ttcccggcgc ggcgggtcag ccgcacgccc gcatcaaggc cagccacttc     840
atccaggagg acagcggaac cgaactcgcc gaacgcatgc tctcctggca gcaggcaacg     900
taa                                                                   903

<210> SEQ ID NO 10
<211> LENGTH: 300
<212> TYPE: PRT
<213> ORGANISM: Mycobacterium bovis

<400> SEQUENCE: 10

Met Asp Val Leu Arg Thr Pro Asp Ser Arg Phe Glu His Leu Val Gly
1               5                   10                  15
```

-continued

```
Tyr Pro Phe Ala Pro His Tyr Val Asp Val Thr Ala Gly Asp Thr Gln
            20                  25                  30

Pro Leu Arg Met His Tyr Val Asp Glu Gly Pro Gly Asp Gly Pro Pro
        35                  40                  45

Ile Val Leu Leu His Gly Glu Pro Thr Trp Ser Tyr Leu Tyr Arg Thr
    50                  55                  60

Met Ile Pro Pro Leu Ser Ala Ala Gly His Arg Val Leu Ala Pro Asp
65                  70                  75                  80

Leu Ile Gly Phe Gly Arg Ser Asp Lys Pro Thr Arg Ile Glu Asp Tyr
                85                  90                  95

Thr Tyr Leu Arg His Val Glu Trp Val Thr Ser Trp Phe Glu Asn Leu
            100                 105                 110

Asp Leu His Asp Val Thr Leu Phe Val Gln Asp Trp Gly Ser Leu Ile
        115                 120                 125

Gly Leu Arg Ile Ala Ala Glu His Gly Asp Arg Ile Ala Arg Leu Val
    130                 135                 140

Val Ala Asn Gly Phe Leu Pro Ala Ala Gln Gly Arg Thr Pro Leu Pro
145                 150                 155                 160

Phe Tyr Val Trp Arg Ala Phe Ala Arg Tyr Ser Pro Val Leu Pro Ala
                165                 170                 175

Gly Arg Leu Val Asn Phe Gly Thr Val His Arg Val Pro Ala Gly Val
            180                 185                 190

Arg Ala Gly Tyr Asp Ala Pro Phe Pro Asp Lys Thr Tyr Gln Ala Gly
        195                 200                 205

Ala Arg Ala Phe Pro Arg Leu Val Pro Thr Ser Pro Asp Asp Pro Ala
    210                 215                 220

Val Pro Ala Asn Arg Ala Ala Trp Glu Ala Leu Gly Arg Trp Asp Lys
225                 230                 235                 240

Pro Phe Leu Ala Ile Phe Gly Tyr Arg Asp Pro Ile Leu Gly Gln Ala
                245                 250                 255

Asp Gly Pro Leu Ile Lys His Ile Pro Gly Ala Ala Gly Gln Pro His
            260                 265                 270

Ala Arg Ile Lys Ala Ser His Phe Ile Gln Glu Asp Ser Gly Thr Glu
        275                 280                 285

Leu Ala Glu Arg Met Leu Ser Trp Gln Gln Ala Thr
    290                 295                 300

<210> SEQ ID NO 11
<211> LENGTH: 861
<212> TYPE: DNA
<213> ORGANISM: Mycobacterium bovis

<400> SEQUENCE: 11
atgagcatcg atttcacgcc ggatccgcag ctgtacccgt tcgagtcgcg ctggttcgac      60
agctcgcgtg gacgcatcca ctacgtcgac gagggcacgg gtccgccgat cctgttgtgt     120
cacggcaacc cgacgtggag tttcctgtat cgggacatca tcgtcgcact gcgggaccgt     180
ttccgttgtg tggctccgga ttatctgggt ttcgggttat cggagcgtcc ctcgggattc     240
gggtaccaga tcgacgagca cgcgcgggtg atcggcgaat tcgtcgatca cctgggcctg     300
gaccgctacc tgagcatggg tcaggactgg ggtggcccga tcagcatggc ggtcgctgtc     360
gagcgtgccg accgggtccg cggcgtcgtg ttgggcaaca cgtggttctg gccggcggac     420
acgctggcga tgaaggcctt cagcagggtg atgtccagcc cgccagtgca gtacgcgatc     480
ttacggcgca acttctttgt cgagcgcttg atacccgcgg gaaccgagca ccggccgagt     540
```

-continued

```
agcgcggtga tggcgcacta ccgggcggtg cagcccaacg ccgcggcacg ccgaggcgta    600
gccgagatgc ccaaacagat cctggccgcc cgtcccctgc tggcacggct cgcccgggag    660
gtgccagcca cgctgggcac caagcccacc ctgttgattt gggggatgaa ggatgtcgca    720
ttcaggccga aaacgattat ccccagactg agtgcgacat ttcccgacca cgtcctggtg    780
gagctgccca acgccaaaca cttcatccag gaggacgccc ccgaccggat cgccgccgcg    840
atcattgagc gcttcggctg a                                              861

<210> SEQ ID NO 12
<211> LENGTH: 286
<212> TYPE: PRT
<213> ORGANISM: Mycobacterium bovis

<400> SEQUENCE: 12

Met Ser Ile Asp Phe Thr Pro Asp Pro Gln Leu Tyr Pro Phe Glu Ser
1               5                   10                  15

Arg Trp Phe Asp Ser Ser Arg Gly Arg Ile His Tyr Val Asp Glu Gly
            20                  25                  30

Thr Gly Pro Pro Ile Leu Leu Cys His Gly Asn Pro Thr Trp Ser Phe
        35                  40                  45

Leu Tyr Arg Asp Ile Ile Val Ala Leu Arg Asp Arg Phe Arg Cys Val
    50                  55                  60

Ala Pro Asp Tyr Leu Gly Phe Gly Leu Ser Glu Arg Pro Ser Gly Phe
65                  70                  75                  80

Gly Tyr Gln Ile Asp Glu His Ala Arg Val Ile Gly Glu Phe Val Asp
                85                  90                  95

His Leu Gly Leu Asp Arg Tyr Leu Ser Met Gly Gln Asp Trp Gly Gly
            100                 105                 110

Pro Ile Ser Met Ala Val Ala Val Glu Arg Ala Asp Arg Val Arg Gly
        115                 120                 125

Val Val Leu Gly Asn Thr Trp Phe Trp Pro Ala Asp Thr Leu Ala Met
    130                 135                 140

Lys Ala Phe Ser Arg Val Met Ser Ser Pro Pro Val Gln Tyr Ala Ile
145                 150                 155                 160

Leu Arg Arg Asn Phe Phe Val Glu Arg Leu Ile Pro Ala Gly Thr Glu
                165                 170                 175

His Arg Pro Ser Ser Ala Val Met Ala His Tyr Arg Ala Val Gln Pro
            180                 185                 190

Asn Ala Ala Ala Arg Arg Gly Val Ala Glu Met Pro Lys Gln Ile Leu
        195                 200                 205

Ala Ala Arg Pro Leu Leu Ala Arg Leu Ala Arg Glu Val Pro Ala Thr
    210                 215                 220

Leu Gly Thr Lys Pro Thr Leu Leu Ile Trp Gly Met Lys Asp Val Ala
225                 230                 235                 240

Phe Arg Pro Lys Thr Ile Ile Pro Arg Leu Ser Ala Thr Phe Pro Asp
                245                 250                 255

His Val Leu Val Glu Leu Pro Asn Ala Lys His Phe Ile Gln Glu Asp
            260                 265                 270

Ala Pro Asp Arg Ile Ala Ala Ala Ile Ile Glu Arg Phe Gly
        275                 280                 285

<210> SEQ ID NO 13
<211> LENGTH: 987
<212> TYPE: DNA
```

<213> ORGANISM: Rhodopirellula baltica

<400> SEQUENCE: 13

```
ttgagttgcc gcctctcgtc aaatcgccgc ggatcgtcga aactagccgc catgacgaat      60
cttgctagcg atctgtttcc ccacccgtcg tcggaattgt ccatcgacgg tcacacgctg     120
cgctacatcg atacggcggc cagctctgac atcccgagtt ccgcggtcgg atcctccgat     180
ggcgagccaa cgtttctttg tgtgcatggc aatccgacgt ggagctttta ctaccggcga     240
atcatcgagc ggtatggcaa gcagcaacga gtgatcgcgg tcgatcacat cggttgtggt     300
cgcagcgaca aaccatcgga agacgaattc ccgtacacga tggccgcgca tcgagacaac     360
ctgattcggt tggtcgacga gttggatctg aagaacgtga tcctgatcgc tcacgattgg     420
ggtggtgcga ttggtttgtc agccatgcat gctcgccgag accgcttggc tgggattggg     480
ttgctgaaca cggctgcgtt cccaccgccg tacatgcctc agcgaattgc cgcgtgccgg     540
atgccggtgt gggaactcc cgcagttcgc ggattgaact tgttcgcacg gccgcggtc      600
accatggcca tgtcgcgtac gaagatgaaa cccgatgtcg cagcgggatt gctggctccc     660
tatgacaatt ggaagaaccg agtcgcaatc gatcggttcg ttcgcgacat tcctttgaat     720
gattcgcatc ccacgatgaa gactcttcgg cagctggagt ccgatctgcc ggacctggca     780
tcgctaccca tctctttgat ttggggaatg aaggattggt gttttcgacc ggaatgtctg     840
cgacgtttcc aatccgtttg gcccgacgcg gaagtcacgg aactggcgac gaccggtcac     900
tatgtgatcg aagactcgcc cgaagaaacc ttggccgcga ttgattcatt gctcgcccgc     960
gtcaaggaac gcatcggtgc ggcgtga                                         987
```

<210> SEQ ID NO 14
<211> LENGTH: 328
<212> TYPE: PRT
<213> ORGANISM: Rhodopirellula baltica

<400> SEQUENCE: 14

```
Met Ser Cys Arg Leu Ser Ser Asn Arg Arg Gly Ser Ser Lys Leu Ala
1               5                   10                  15
Ala Met Thr Asn Leu Ala Ser Asp Leu Phe Pro His Pro Ser Ser Glu
            20                  25                  30
Leu Ser Ile Asp Gly His Thr Leu Arg Tyr Ile Asp Thr Ala Ala Ser
        35                  40                  45
Ser Asp Ile Pro Ser Ser Ala Val Gly Ser Ser Asp Gly Glu Pro Thr
    50                  55                  60
Phe Leu Cys Val His Gly Asn Pro Thr Trp Ser Phe Tyr Tyr Arg Arg
65                  70                  75                  80
Ile Ile Glu Arg Tyr Gly Lys Gln Gln Arg Val Ile Ala Val Asp His
                85                  90                  95
Ile Gly Cys Gly Arg Ser Asp Lys Pro Ser Glu Asp Glu Phe Pro Tyr
            100                 105                 110
Thr Met Ala Ala His Arg Asp Asn Leu Ile Arg Leu Val Asp Glu Leu
        115                 120                 125
Asp Leu Lys Asn Val Ile Leu Ile Ala His Asp Trp Gly Gly Ala Ile
    130                 135                 140
Gly Leu Ser Ala Met His Ala Arg Arg Asp Arg Leu Ala Gly Ile Gly
145                 150                 155                 160
Leu Leu Asn Thr Ala Ala Phe Pro Pro Pro Tyr Met Pro Gln Arg Ile
                165                 170                 175
```

```
Ala Ala Cys Arg Met Pro Val Leu Gly Thr Pro Ala Val Arg Gly Leu
            180                 185                 190

Asn Leu Phe Ala Arg Ala Ala Val Thr Met Ala Met Ser Arg Thr Lys
        195                 200                 205

Met Lys Pro Asp Val Ala Ala Gly Leu Leu Ala Pro Tyr Asp Asn Trp
    210                 215                 220

Lys Asn Arg Val Ala Ile Asp Arg Phe Val Arg Asp Ile Pro Leu Asn
225                 230                 235                 240

Asp Ser His Pro Thr Met Lys Thr Leu Arg Gln Leu Glu Ser Asp Leu
                245                 250                 255

Pro Asp Leu Ala Ser Leu Pro Ile Ser Leu Ile Trp Gly Met Lys Asp
            260                 265                 270

Trp Cys Phe Arg Pro Glu Cys Leu Arg Arg Phe Gln Ser Val Trp Pro
        275                 280                 285

Asp Ala Glu Val Thr Glu Leu Ala Thr Thr Gly His Tyr Val Ile Glu
    290                 295                 300

Asp Ser Pro Glu Glu Thr Leu Ala Ala Ile Asp Ser Leu Leu Ala Arg
305                 310                 315                 320

Val Lys Glu Arg Ile Gly Ala Ala
                325

<210> SEQ ID NO 15
<211> LENGTH: 906
<212> TYPE: DNA
<213> ORGANISM: Mycobacterium avium

<400> SEQUENCE: 15
atgcatgtgc tgcgaacccc ggactcccga ttcgaaaacc tggaggacta cccgttcgtg      60
gcgcattatc tcgacgtcac cgcgcgcgac acccggccgc ttcgcatgca ctacctggac     120
gaggggccga tcgacgggcc accgatcgtg ctgctgcacg gcgagcccac ctggagctac     180
ctgtaccgca ccatgatcac gccgctgacc gacgccggaa accgggtgct ggcacccgac     240
ttgatcggct tcggccggtc ggacaagccc agcggatcg aggactactc ctaccagcgg      300
cacgtggact gggtggtctc ctggttcgaa cacctcaacc tcagcgacgt cacgctgttc     360
gtgcaggact ggggatcatt gatcgggctg cgcatcgccg ccgagcagcc cgaccgggtg     420
ggacggctgg tggtggccaa cggctttctt cccaccgcgc agcgacgcac cccgcccgcc     480
ttctacgcgt ggcgagcctt cgcgcgctac tcccccgtgc tgcccgccgg ccgcatcgtc     540
agcgtcggga ccgtccgccg ggtttcgtcc aaggtgcgtg ccggctacga cgcgcccttc     600
cccgacaaga cgtatcaggc cggggcgcgg gcatttccgc aactggtgcc cacctcgccg     660
gccgatcccg cgattccggc caaccgcaag gcgtgggaag ccctcggccg ctgggaaaaa     720
ccgttcctgg ccatcttcgg cgcccgcgac ccatcctcg gccacgcgga cagtccgctg      780
atcaagcaca ttccgggcgc gcgggccaa ccgcacgccc gcatcaacgc cagtcacttc      840
atccaggagg accgcggacc tgaactggcc gaacgcatcc tgtcctggca gcaggcgctg     900
ctctga                                                               906

<210> SEQ ID NO 16
<211> LENGTH: 301
<212> TYPE: PRT
<213> ORGANISM: Mycobacterium avium

<400> SEQUENCE: 16

Met His Val Leu Arg Thr Pro Asp Ser Arg Phe Glu Asn Leu Glu Asp
```

```
1               5                   10                  15
Tyr Pro Phe Val Ala His Tyr Leu Asp Val Thr Ala Arg Asp Thr Arg
                20                  25                  30
Pro Leu Arg Met His Tyr Leu Asp Glu Gly Pro Ile Asp Gly Pro Pro
                35                  40                  45
Ile Val Leu Leu His Gly Glu Pro Thr Trp Ser Tyr Leu Tyr Arg Thr
 50                 55                  60
Met Ile Thr Pro Leu Thr Asp Ala Gly Asn Arg Val Leu Ala Pro Asp
 65                 70                  75                  80
Leu Ile Gly Phe Gly Arg Ser Asp Lys Pro Ser Arg Ile Glu Asp Tyr
                85                  90                  95
Ser Tyr Gln Arg His Val Asp Trp Val Val Ser Trp Phe Glu His Leu
                100                 105                 110
Asn Leu Ser Asp Val Thr Leu Phe Val Gln Asp Trp Gly Ser Leu Ile
                115                 120                 125
Gly Leu Arg Ile Ala Ala Glu Gln Pro Asp Arg Val Gly Arg Leu Val
                130                 135                 140
Val Ala Asn Gly Phe Leu Pro Thr Ala Gln Arg Thr Pro Pro Ala
145                 150                 155                 160
Phe Tyr Ala Trp Arg Ala Phe Ala Arg Tyr Ser Pro Val Leu Pro Ala
                165                 170                 175
Gly Arg Ile Val Ser Val Gly Thr Val Arg Arg Val Ser Ser Lys Val
                180                 185                 190
Arg Ala Gly Tyr Asp Ala Pro Phe Pro Asp Lys Thr Tyr Gln Ala Gly
                195                 200                 205
Ala Arg Ala Phe Pro Gln Leu Val Pro Thr Ser Pro Ala Asp Pro Ala
                210                 215                 220
Ile Pro Ala Asn Arg Lys Ala Trp Glu Ala Leu Gly Arg Trp Glu Lys
225                 230                 235                 240
Pro Phe Leu Ala Ile Phe Gly Ala Arg Asp Pro Ile Leu Gly His Ala
                245                 250                 255
Asp Ser Pro Leu Ile Lys His Ile Pro Gly Ala Ala Gly Gln Pro His
                260                 265                 270
Ala Arg Ile Asn Ala Ser His Phe Ile Gln Glu Asp Arg Gly Pro Glu
                275                 280                 285
Leu Ala Glu Arg Ile Leu Ser Trp Gln Gln Ala Leu Leu
                290                 295                 300

<210> SEQ ID NO 17
<211> LENGTH: 909
<212> TYPE: DNA
<213> ORGANISM: Bradyrhizobium elkanii

<400> SEQUENCE: 17
atgaccatat ccgccgatat cagcctgcat catcgcgccg tgctcgggag cacgatggcc      60
tatcgcgaga ccggccgcag cgacgcgccg catgtgctgt tcctgcacgg caatccgacg     120
tcgtcctaca tctggcgcaa catcatgccg ctggtcgccc ccgtcgggca ttgcatcgcg     180
cccgacctga tcggctacgg ccaatccggc aagcccgaca tcagctatcg cttcttcgac     240
caggcggact atctcgacgc gctgatcgac gaactcggca tcgcctcggc ctatctcgtc     300
gcccaggact ggggcacggc gcttgccttc cacctcgcgg cacgccgtcc gcaactggtg     360
cgcgggctcg ctttcatgga gttcatccgc ccgatgcgcg attggtcgga cttccaccag     420
cacgacgccg cgcgggagac gttccggaaa ttccgcacgc cgggcgtggg cgaggcgatg     480
```

-continued

```
atcctcgata caatgcgtt cgtcgaacgc gtgctgcccg gctcgatcct gcgcacgctc      540
agcgaggagg agatggccgc ctaccgcgcg ccgtttgcga cgcgcgagag ccgcatgccg      600
accttgatgc tgccgcgcga actgccgatc gcgggcgagc cggccgacgt tactcaggcg      660
ctcacggcgg cgcatgccgc gctcgcggca tcgacctatc cgaagctgct gtttgttggg      720
tcgcccgggg cgctggtgtc accggccttt gccgccgaat cgccaagac gctcaagcat      780 tgcgcggtca ttcaactcgg cgcgggcggg cattatctgc aggaggatca tccggaggcg      840
atcggccgct ctgtggccgg ctggatcgcc ggcatcgagg ccgcctccgc gcagcgccat      900
gccgcatga                                                            909
```

<210> SEQ ID NO 18
<211> LENGTH: 302
<212> TYPE: PRT
<213> ORGANISM: Bradyrhizobium elkanii

<400> SEQUENCE: 18

```
Met Thr Ile Ser Ala Asp Ile Ser Leu His His Arg Ala Val Leu Gly
1               5                   10                  15

Ser Thr Met Ala Tyr Arg Glu Thr Gly Arg Ser Asp Ala Pro His Val
                20                  25                  30

Leu Phe Leu His Gly Asn Pro Thr Ser Ser Tyr Ile Trp Arg Asn Ile
            35                  40                  45

Met Pro Leu Val Ala Pro Val Gly His Cys Ile Ala Pro Asp Leu Ile
        50                  55                  60

Gly Tyr Gly Gln Ser Gly Lys Pro Asp Ile Ser Tyr Arg Phe Phe Asp
65                  70                  75                  80

Gln Ala Asp Tyr Leu Asp Ala Leu Ile Asp Glu Leu Gly Ile Ala Ser
                85                  90                  95

Ala Tyr Leu Val Ala Gln Asp Trp Gly Thr Ala Leu Ala Phe His Leu
            100                 105                 110

Ala Ala Arg Arg Pro Gln Leu Val Arg Gly Leu Ala Phe Met Glu Phe
        115                 120                 125

Ile Arg Pro Met Arg Asp Trp Ser Asp Phe His Gln His Asp Ala Ala
130                 135                 140

Arg Glu Thr Phe Arg Lys Phe Arg Thr Pro Gly Val Gly Glu Ala Met
145                 150                 155                 160

Ile Leu Asp Asn Asn Ala Phe Val Glu Arg Val Leu Pro Gly Ser Ile
                165                 170                 175

Leu Arg Thr Leu Ser Glu Glu Glu Met Ala Ala Tyr Arg Ala Pro Phe
            180                 185                 190

Ala Thr Arg Glu Ser Arg Met Pro Thr Leu Met Leu Pro Arg Glu Leu
        195                 200                 205

Pro Ile Ala Gly Glu Pro Ala Asp Val Thr Gln Ala Leu Thr Ala Ala
    210                 215                 220

His Ala Ala Leu Ala Ala Ser Thr Tyr Pro Lys Leu Leu Phe Val Gly
225                 230                 235                 240

Ser Pro Gly Ala Leu Val Ser Pro Ala Phe Ala Ala Glu Phe Ala Lys
                245                 250                 255

Thr Leu Lys His Cys Ala Val Ile Gln Leu Gly Ala Gly Gly His Tyr
            260                 265                 270

Leu Gln Glu Asp His Pro Glu Ala Ile Gly Arg Ser Val Ala Gly Trp
        275                 280                 285
```

```
Ile Ala Gly Ile Glu Ala Ala Ser Ala Gln Arg His Ala Ala
        290                 295                 300
```

\<210\> SEQ ID NO 19
\<211\> LENGTH: 915
\<212\> TYPE: DNA
\<213\> ORGANISM: Artificial Sequence
\<220\> FEATURE:
\<223\> OTHER INFORMATION: Chemically Synthesized. Recombinant gene of the
       modified protein was obtained by using QuickChange(tm)
       Site-Directed Mutagenesis Kit (Stratagene, USA).

\<400\> SEQUENCE: 19

```
atgtcagaaa tcggtacagg cttccccttc gaccccatt atgtggaagt cctgggcgag     60
cgtatgcact acgtcgatgt tggaccgcgg gatggcacgc ctgtgctgtt cctgcacggt    120
aacccgacct cgtcctacct gtggcgcaac atcatcccgc atgtagcacc gagtcatcgg    180
tgcattgctc cagacctgat cgggatggga aaatcggaca aaccagacct cgattatttc    240
ttcgacgacc acgtccgcta cctcgatgcc ttcatcgaag ccttgggttt ggaagaggtc    300
gtcctggtca tccacgactg gggctcagct ctcggattcc actgggccaa gcgcaatccg    360
gaacgggtca aggtattgc atgtatggaa ttcatccggc tatcccgac gtgggacgaa     420 tttcaccata ccgaagttgc agaagagcaa gatcacgcgg aagccgcccg tgagaccttc    480
caggccttcc ggaccgccga cgtcggccga gagttgatca tcgatcagaa cgctttcatc    540
gagcgtgtgc tcccgggagg cgtcgtccgt ccgcttacgg aggtcgagat ggaccactat    600
cgcgagccct cctcaagcc tgttaccga gagccactgt ggcgattccc caacgagctg     660
cccatcgccg gtgagcccgc gaacatcgtc gcgctcgtcg aggcatacat gaactggctg    720
caccagtcac ctgtcccgaa gttgttgttc tggggcacac ccggcgcact gatcccccg     780 gccgaagccg cgagacttgc cgaaagcctc cccaactgca agacagtgga catcggcccg    840
ggattgcact acctccagga agacaacccg gaccttatcg gcagtgagat cgcgcgctgg    900
ctccccgcac tctga                                                    915
```

\<210\> SEQ ID NO 20
\<211\> LENGTH: 304
\<212\> TYPE: PRT
\<213\> ORGANISM: Artificial Sequence
\<220\> FEATURE:
\<223\> OTHER INFORMATION: Chemically Synthesized. Recombinant gene of the
       modified protein was obtained by using QuickChange(tm)
       Site-Directed Mutagenesis Kit (Stratagene, USA).

\<400\> SEQUENCE: 20

```
Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110
```

-continued

```
Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Phe His His Thr
        130                 135                 140

Glu Val Ala Glu Glu Gln Asp His Ala Glu Ala Ala Arg Glu Thr Phe
145                 150                 155                 160

Gln Ala Phe Arg Thr Ala Asp Val Gly Arg Glu Leu Ile Ile Asp Gln
                165                 170                 175

Asn Ala Phe Ile Glu Arg Val Leu Pro Gly Gly Val Val Arg Pro Leu
            180                 185                 190

Thr Glu Val Glu Met Asp His Tyr Arg Glu Pro Phe Leu Lys Pro Val
        195                 200                 205

Asp Arg Glu Pro Leu Trp Arg Phe Pro Asn Glu Leu Pro Ile Ala Gly
        210                 215                 220

Glu Pro Ala Asn Ile Val Ala Leu Val Glu Ala Tyr Met Asn Trp Leu
225                 230                 235                 240

His Gln Ser Pro Val Pro Lys Leu Leu Phe Trp Gly Thr Pro Gly Ala
                245                 250                 255

Leu Ile Pro Pro Ala Glu Ala Ala Arg Leu Ala Glu Ser Leu Pro Asn
            260                 265                 270

Cys Lys Thr Val Asp Ile Gly Pro Gly Leu His Tyr Leu Gln Glu Asp
        275                 280                 285

Asn Pro Asp Leu Ile Gly Ser Glu Ile Ala Arg Trp Leu Pro Ala Leu
        290                 295                 300
```

METHOD OF PRODUCTION OF OPTICALLY ACTIVE HALOHYDROCARBONS AND ALCOHOLS USING HYDROLYTIC DEHALOGENATION CATALYSED BY HALOALKANE DEHALOGENASES

CROSS-REFERENCE TO RELATED APPLICATION

This is a continuation-in-part of application Ser. No. 11/793,635 filed Jun. 20, 2007 and incorporated here by reference.

FIELD OF THE INVENTION

This invention relates to method of production of optically active haloalkanes and alcohols using hydrolytic dehalogenation. The Sequence Listing which is incorporated here by reference, appears after the Abstract.

STATE OF THE ART

Enzymes are catalysts of biological systems that determine the patterns of chemical transformations. The most striking characteristics of enzymes are their catalytic power and specificity. They are highly effective catalysts for an enormous diversity of chemical reactions because of their capacity to specifically bind a very wide range of molecules. The enzymes catalyse reactions by destabilizing substrate or by stabilizing transition state and determining which one of several potential chemical reactions actually will take place.

The manufacture of enantiomerically pure compounds has become an expanding area of fine chemical industry. When pharmaceuticals, agrochemicals, food additives and their synthetic intermediates are marketed as single enantiomers, high enantiomeric purities, typically enantiomeric excess (e.e.)>98%, are required (enantiomeric excess is derived from the concentration of the two enantiomenrs $c^R$ and $c^S$; Equation 1).

$$e.e. = \left| \frac{c^R - c^S}{c^R + c^S} \right| \quad \text{(Eq. 1)}$$

$$E = \frac{(k_{cat}/K_m)_R}{(k_{cat}/K_m)_S} \quad \text{(Eq. 2)}$$

Enzyme-catalyzed reactions have become popular alternatives to classical chemistry for their high selectivity and activity under mild reaction conditions, and several industrial processes using enzymes as catalysts are already in use. Clearly, the enantioselective performance of the catalyst is the single most important factor for the success of such a process (evaluation of this property is facilitated by the use of enantiomeric ratio (E); E-values can be expressed as ratio $k_{cat}/K_m$ of the rate constants $k_{cat}$ for catalysis and the Michaelis-Menten constants $K_m$ of the two enantiomers; Equation 2).

Chemical transformation of halogenated compounds is important from both the environmental and synthetic point of view. Six major pathways for enzymatic transformation of halogenated compounds have been described: (i) oxidation, (ii) reduction, (iii) dehydrohalogenation, (iv) hydration, (v) methyl transfer and (vi) hydrolytic, glutathione-dependent and intramolecular substitution. Redox enzymes are responsible for the replacement of the halogen by a hydrogen atom and for oxidative degradation. Elimination of hydrogen halide leads to the formation of an alkene, which is further degraded by oxidation. The enzyme-catalysed formation of an epoxide from a halohydrin and the hydrolytic replacement of a halide by hydroxyl functionality take place in a stereospecific manner and are therefore of high synthetic interest [Falber, K. (2000) Biotransformations in Organic Chemistry, Springer-Verlag, Heidelberg, 450].

Haloalkane dehalogenases (the enzyme code number EC 3.8.1.5) are enzymes able to remove halogen from halogenated aliphatic compounds by a hydrolytic replacement, forming the corresponding alcohols [Janssen, D. B., Pries, F., and Van der Ploeg, J. R. (1994) Annual Review of Microbiology 48, 163-191]. Hydrolytic dehalogenation proceeds by formal nucleophilic substitution of the halogen atom with a hydroxyl ion. The mechanism of hydrolytic dehalogenation catalysed by the haloalkane dehalogenase enzymes (EC 3.8.1.5) is shown in Eq. 3. A co-factor or a metal ion is not required for the enzymatic activity of haloalkane dehalogenases. The reaction is initiated by binding of the substrate in the active site with the halogen in the halide-binding site. The binding step is followed by a nucleophilic attack of aspartic acid (Asp) on the carbon atom to which the halogen is bound, leading to cleavage of the carbon-halogen bond and formation of alkyl-enzyme intermediate. The intermediate is subsequently hydrolysed by activated water, with histidine (His) acting as a base catalyst, with formation of enzyme-product complex.

Asp or glutamic acid (Glu) keeps H is in proper orientation and stabilises a positive charge that develops on H is imidazole ring during the reaction. The final step is release of the products.

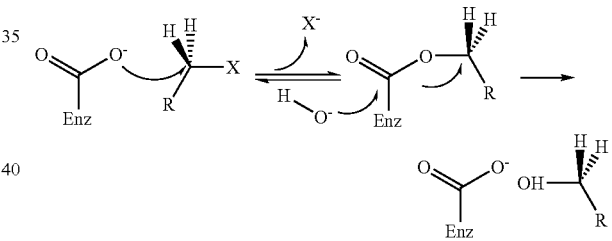

Eq. 3—Reaction mechanism for the hydrolytic dehalogenation by haloalkane dehalogenases (EC 3.8.1.5)

The first haloalkane dehalogenase has been isolated from the bacterium Xanthobacter autotrophicus GJ10 in 1985 [Janssen, D. B., Scheper, A., Dijkhuizen, L., and Witholt, B. (1985) Applied and Environmental Microbiology 49, 673-677; Keuning, S., Janssen, D. B., and Witholt, B. (1985) Journal of Bacteriology 163, 635-639]. Since then, a large number of haloalkane dehalogenases has been isolated from contaminated environments [Scholtz, R., Leisinger, T., Suter, F., and Cook, A. M. (1987) Journal of Bacteriology 169, 5016-5021; Yokota, T., Omori, T., and Kodama, T. (1987) Journal of Bacteriology 169, 4049-4054; Janssen, D. B., Gerritse, J., Brackman, J., Kalk, C., Jager, D., and Witholt, B. (1988) European Journal of Biochemistry 171, 67-92; Sallis, P. J., Armfield, S. J., Bull, A. T., and Hardman, D. J. (1990) Journal of General Microbiology 136, 115-120; Nagata, Y., Miyauchi, K., Damborsky, J., Manova, K., Ansorgova, A., and Takagi, M. (1997) Applied and Environmental Microbiology 63, 3707-3710; Poelarends, G. J., Wilkens, M., Larkin, M. J., van Elsas, J. D., and Janssen, D. B. (1998) Applied and Environmental Microbiology 64, 2931-2936]. More recently, hydrolytic dehalogenating activity of several species of genus

*Mycobacterium* isolated from clinical material [Jesenska, A., Sedlacek, I., and Damborsky, J. (2000) *Applied and Environmental Microbiology* 66, 219-222] have been reported, and haloalkane dehalogenases have been subsequently isolated from pathogenic bacteria [Jesenska, A., Bartos, M., Czernekova, V., Rychlik, I., Pavlik, I., and Damborsky, J. (2002) *Applied and Environmental Microbiology* 68, 3724-3730]. Haloalkane dehalogenases can be also found also the rhizobial strains colonizing roots of plants [Sato, Y., Monincova, M., Chaloupkova, R., Prokop, Z., Ohtsubo, Y., Minamisawa, K., Tsuda, M., Damborsky, J., Nagata, Y. *Applied and Environmental Microbiology*, (2005) 71: 4372-4379].

Structurally, haloalkane dehalogenases belong to the α/β-hydrolase fold superfamily [Ollis, D. L., Cheah, E., Cygler, M., Dijkstra, B., Frolow, F., Franken, S. M., Harel, M., Remington, S. J., Silman, I., Schrag, J., Sussman, J. L., Verschueren, K. H. G., and Goldman, A. (1992) *Protein Engineering* 5, 197-211; Nardini, M., and Dijkstra, B. W. (1999) *Current Opinion in Structural Biology* 9, 732-737]. Without exception, haloalkane dehalogenases contain a nucleophile elbow [Damborsky, J. (1998) *Pure and Applied Chemistry* 70, 1375-1383; Damborsky, J., and Koca, J. (1999) *Protein Engineering* 12, 989-998], which is the most conserved structural feature within the α/β-hydrolase fold. The other highly conserved region in haloalkane dehalogenases is the central β-sheet. Its strands, flanked on both sides by α-helices, form the hydrophobic core of the main domain that carries the catalytic triad Asp-His-Asp/Glu. The second domain, consisting solely of α-helices, lies like a cap on top of the main domain. Residues on the interface of the two domains form the active site. Whereas there is significant similarity in the catalytic core, the sequence and structure of the cap domain diverge considerably among different dehalogenase. The cap domain is proposed to play a prominent role in determining substrate specificity [Pries, F., Van den Wijngaard, A. J., Bos, R., Pentenga, M., and Janssen, D. B. (1994) Journal of Biological Chemistry 269, 17490-17494; Kmunicek, J., Luengo, S., Gago, F., Ortiz, A. R., Wade, R. C., and Damborsky, J. (2001) *Biochemistry* 40, 8905-8917].

A number of haloalkane dehalogenases from different bacteria have been biochemically characterised. A principal component analysis of activity data indicated the presence of three specificity classes within this family of enzymes [Nagata, Y., Miyauchi, K., Damborsky, J., Manova, K., Ansorgova, A., and Takagi, M. (1997) *Applied and Environmental Microbiology* 63, 3707-3710; Damborsky, J., and Koca, J. (1999) *Protein Engineering* 12, 989-998; Damborsky, J., Nyandoroh, M. G., Nemec, M., Holoubek, I., Bull, A. T., and Hardman, D. J. (1997) *Biotechnology and Applied Biochemistry* 26, 19-25]. Three haloalkane dehalogenases representing these different classes have been isolated and structurally characterised in atomic detail so far: the haloalkane dehalogenase DhlA from *Xantobacter autotrophicus* GJ10 [Keuning, S., Janssen, D. B., and Witholt, B. (1985) *Journal of Bacteriology* 163, 635-639; Franken, S. M., Rozeboom, H. J., Kalk, K. H., and Dijkstra, B. W. (1991) *The EMBO Journal* 10, 1297-1302], the haloalkane dehalogenase DhaA from *Rhodococcus rhodochrous* NCIMB 13064 [Kulakova, A. N., Larkin, M. J., and Kulakov, L. A. (1997) *Microbiology* 143, 109-115; Newman, J., Peat, T. S., Richard, R., Kan, L., Swanson, P. E., Affholter, J. A., Holmes, I. H., Schindler, J. F., Unkefer, C. J., and Terwilliger, T. C. (1999) *Biochemistry* 38, 16105-16114] and the haloalkane dehalogenase LinB from *Sphingomonas paucimobilis* UT26 [Nagata, Y., Miyauchi, K., Damborsky, J., Manova, K., Ansorgova, A., and Takagi, M. (1997) *Applied and Environmental Microbiology* 63, 3707-3710; Marek, J., Vevodova, J., Kuta-Smatanova, I., Nagata, Y., Svensson, L. A., Newman, J., Takagi, M., and Damborsky, J. (2000) *Biochemistry* 39, 14082-14086]. The size, geometry and physico-chemical properties of active sites and entrance tunnels, as well as nature and spatial arrangement of the catalytic residues (catalytic triad, primary and secondary halide-stabilizing residues [Bohac, M., Nagata, Y., Prokop, Z., Prokop, M., Monincova, M., Koca, J., Tsuda, M., and Damborsky, J. (2002) *Biochemistry* 41, 14272-14280] can be related to the substrate specificity, which is different for enzymes representing different classes [Damborsky, J., Rorije, E., Jesenska, A., Nagata, Y., Klopman, G., and Peijnenburg, W. J. G. M. (2001) *Environmental Toxicology and Chemistry* 20, 2681-2689].

Several patent applications concern the dehalogenation methods using dehalogenase enzymes. For instance, the application WO 98/36080 A1 relates to dehalogenases capable of converting the halogenated aliphatic compounds to vicinal halohydrines and DNA sequences encoding polypeptides of enzymes as well as to DNA sequences and the methods of producing the enzymes by placing the expression constructs into host cells. The patent document WO 01/46476 A1 relates to methods of dehalogenation of alkylhalogenes catalyzed by altered hydrolase enzymes under formation of stereoselective or stereospecific reaction products as alcohols, polyols and epoxides. This patent document includes also method of providing altered nucleic acids that encode altered dehalogenase or other hydrolase enzymes. The patent document WO 02/068583 A2 relates to haloalkane dehalogenases and to polynucleotides encoding the haloalkane dehalogenases. In addition, methods of designing new dehalogenases and method of use thereof are also provided. The dehalogenases have increased activity and stability at increased pH and temperature.

Although several patent applications relate to enzymatically catalysed dehalogenation, there has been no report that the specific family of hydrolytic enzymes, haloalkane dehalogenases (EC 3.8.1.5), shows sufficient enantioselectivity or regioselectivity for large-scale production of optically active alcohols. In 2001, Pieters and co-workers [Pieters, R. J., Spelberg, J. H. L., Kellogg, R. M., and Janssen, D. B. (2001) *Tetrahedron Letters* 42, 469-471] have investigated chiral recognition of haloalkane dehalogenases DhlA and DhaA. The magnitude of the chiral recognition was low; a maximum E-value of 9 could be reached after some structural optimization of the substrate. In the beginning of 2004, twenty years after discovery of the first haloalkane dehalogenase, the development of enantioselective dehalogenases for use in industrial biocatalysis was defined as one of the major challenges of the field [Janssen, D. B. (2004) *Current Opinion in Chemical Biology* 8, 150-159].

All the reactions conducted by Pieters and co-workers [Pieters, R. J., Spelberg, J. H. L., Kellogg, R. M., and Janssen, D. B. (2001) *Tetrahedron Letters* 42, 469-471] exhibited low enantioselectivity which is not sufficient for practical applications. Common characteristic of these reactions was the site for nucleophilic attack of dehalogenating enzyme on the chiral molecule. In all cases, the nucleophilic attack took place on the carbon next to the chiral carbon and not directly on the chiral carbon. This fact is obvious from the rules for preferential attack at alpha-carbon atom over beta-carbon atom defined for haloalkane dehalogenases by Damborsky and co-workers [Damborsky, J., Rorije, E., Jesenska, A., Nagata, Y., Klopman, G., Peijnenburg, W. J. G. M. (2001) *Environmental Toxicology and Chemistry* 20: 2681-2689].

DESCRIPTION OF THE INVENTION

Object of the invention is a method of production of optically active halohydrocarbons and alcohols using hydrolytic dehalogenation catalysed by a haloalkane dehalogenase, wherein at least one wild type or modified haloalkane dehalogenase selected from the group of the haloalkane dehalogenases (EC 3.8.1.5) or their mixtures is applied to at least one racemic or prochiral chlorinated, brominated or iodinated compound at the temperature ranged between +10 and +70° C. and pH value between 4.0 and 12.0, in aqueous system or in a monophasic organic solution or in a monophasic organic/aqueous solution or in organic/aqueous biphasic systems.

Another aspect of the invention is the method of production of optically active halohydrocarbons and alcohols, wherein the chlorinated, brominated or iodinated compounds has at least one halogen atom bound directly to the chiral or prochiral carbon and the nucleophilic attack takes place directly on the chiral or prochiral carbon.

A further aspect of the invention is the method of production of optically active halohydrocarbons and alcohols, wherein the haloalkane dehalogenase is at least one wild type or modified haloalkane dehalogenase selected from the group consisting of:
haloalkane dehalogenase DbjA SEQ ID NO: 1, 2,
haloalkane dehalogenase LinB SEQ ID NO: 3, 4,
haloalkane dehalogenase DhaA SEQ ID NO: 5, 6,
haloalkane dehalogenase DmbA SEQ ID NO: 7, 8,
haloalkane dehalogenase DmbB SEQ ID NO: 9, 10,
haloalkane dehalogenase DmbC SEQ ID NO: 11, 12,
haloalkane dehalogenase DrbA SEQ ID NO: 13, 14,
haloalkane dehalogenase DhmA SEQ ID NO: 15, 16,
haloalkane dehalogenase DbeA SEQ ID NO: 17, 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 95% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 90% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 85% to the sequence SEQ ID NO: 2, 4, 6, 8, 10, 12, 14, 16 or 18.

A further aspect of the invention is the method of production of optically active halohydrocarbons and alcohols, wherein the haloalkane dehalogenase is at least one wild type or modified polypeptide with haloalkane dehalogenase activity having the amino acid sequence that corresponds at least in 80% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 75% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 70% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 65% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 60% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 55% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 50% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 45% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 40% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 35% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 30% to the sequence SEQ ID NO: 2, 4, 6, 8, 10, 12, 14, 16 or 18.

Another aspect of the invention is the method of production of optically active halohydrocarbons and alcohols, wherein the haloalkane dehalogenase is at least one wild type or modified polypeptide with haloalkane dehalogenase activity having an amino acid sequence that corresponds at least in 25% to the sequence SEQ ID NO: 2, 4, 6, 8, 10, 12, 14, 16 or 18.

Another aspect of the invention is the method of production of optically active halohydrocarbons and alcohols, wherein it is performed at presence of surfactants to allow using of enhanced reagent concentration.

A further aspect of the invention is the method of production of optically active halohydrocarbons and alcohols, wherein the enzyme halolkane dehalogenase is in soluble or crystalline or lyophilized or precipitated form.

Another aspect of the invention is the method of production of optically active halohydrocarbons and alcohols, wherein the enzyme haloalkane dehalogenase is immobilized by adsorption or ionic binding or covalent attachment onto the surface of a macroscopic carrier material.

A further aspect of the invention is the method of production of optically active halohydrocarbons and alcohols, wherein the enzyme haloalkane dehalogenase is immobilized by cross-linking or confined to a solid matrix or membrane-restricted compartments.

Hydrolytic dehalogenation of broad series of racemic substrates catalysed by the series of enzymes: haloalkane dehalogenases DmbA, DmbB, DmbC from bacterium *Mycobacterium bovis*, DhlA from *Xanthobacter autotrophicus*, DhaA from *Rhodococcus rhodochrous*, DrbA from *Rhodopirellula baltica*, LinB from *Sphingomonas paucimobilis*, DhmA from *Mycobacterium avium*, DbjA from *Bradyrhizobium japonicum* and DbeA from *Bradyrhizobium elkanii* have been conducted. The dehalogenation reactions were performed with both: (i) substrates carrying halogens on non-chiral carbon and (ii) newly also the substrates carrying halogen substituent directly on the chiral carbon. The results showed that the magnitude of the chiral recognition was low for all the substrates where the dehalogenation took place on a non-chiral carbon (Table 1), which was in correspondence with the previous observations of Pieters and co-workers [Pieters, R. J., Spelberg, J. H. L., Kellogg, R. M., and Janssen, D. B. (2001) *Tetrahedron Letters* 42, 469-471]. Newly, excellent enantioselectivity with haloalkane dehalogenases DmbA, DmbB, DmbC, DbjA, DhaA, DrbA, DhmA and LinB was observed in the reactions taking place directly on the chiral carbon, e.g., methyl-2-bromopropionate, ethyl-2-bromopropionate, ethyl-2-bromobutyrate, 3-bromo-2-butanone and 2-bromopropiophenone.

This observation demonstrated for the first time that the proteins from the family of haloalkane dehalogenases (EC 3.8.1.5) can possess high enantioselectivity sufficient for practical industrial application. We discovered that an essential precondition for high enantioselectivity of haloalkane dehalogenases is the nucleophilic attack taking place directly on a chiral carbon (chiral centre) of converted molecule.

TABLE 1

Examples of chiral recognition, hydrolytic dehalogenation of selected racemic substrates catalyzed by haloalkane dehalogenases DhlA, DhaA, LinB and DbjA.

| | E-values | | | |
|---|---|---|---|---|
| Substrate | DhlA | DhaA | LinB | DbjA |
| methyl 2-bromopropionate | n.a. | 68 | 52 | >200 |
| ethyl 2-bromopropionate | n.a. | 59 | 97 | 194 |
| ethyl 2-bromobutyrate | n.a. | >200 | >200 | >200 |
| 3-bromo-2-butanone | n.a. | >200 | 3 | >200 |
| 2-bromopropiophenone | n.a. | >200 | 13 | >200 |
| methyl 2,4-dibromobutyrate | 1.6 | 1 | 1.9 | 1.3 |
| 2-bromopentane | 5.5 | 7 | 16 | 145 |
| 2-bromohexane | n.d. | 4 | 12 | 35 |
| 2-bromoheptane | 2.4 | 2.9 | 2.8 | 28 |
| 1,2-dichloropropane | 2 | n.d. | n.d. | n.d. |
| 1,2-dibromopropane | 3 | 1.3 | 1.3 | 2.6 |
| 1,2-dibromobutane | 1.1 | 2 | 10 | 2.7 |
| 1,2-dichlorobutane | n.d. | n.d. | n.d. | n.d. |
| 1,3-dibromobutane | 2 | 1.3 | 4.6 | 1.4 |
| 1,3-dichlorobutane | 2.8 | 1.6 | 2.6 | 1.0 |
| 1-bromo-3-chloro-2-methylpropane | 1.8 | 1.7 | 1.8 | 1.4 |

TABLE 1-continued

Examples of chiral recognition, hydrolytic dehalogenation of selected racemic substrates catalyzed by haloalkane dehalogenases DhlA, DhaA, LinB and DbjA.

| | E-values | | | |
|---|---|---|---|---|
| Substrate | DhlA | DhaA | LinB | DbjA |
| 1,2-dibromo-3,3-dimethylbutane | n.d. | n.d. | 1.1 | n.d. |
| epibromohydrine | 1.4 | 1.2 | 1.1 | 1.9 | n.d. . . . not detected (activity < 0.2 nM · s$^{-1}$ · mg$^{-1}$ of enzyme)
n.a. . . . not analyzed These results indicate that hydrolytic dehalogenation catalysed by the enzymes haloalkane dehalogenases (EC 3.8.1.5) has high potential to produce optically active haloalkanes, haloalcohols, alcohols or diols with high optical purity.

By the method of the present invention, racemic reagents or prochiral compounds, e.g., haloalkanes, haloalcohols, halopolyols, are converted enantioselectively or enantiospecifically by hydrolytic dehalogenation taking place directly on chiral or prochiral carbon during the reaction catalysed by the enzyme haloalkane dehalogenase to provide optically active compounds with high purity, which can be used as medicaments, agrochemicals, food additives, cosmetics or ferroelectric liquid crystals or as an intermediate thereof. In general, the method includes hydrolytic dehalogenation of one or more chiral or prochiral reagents yielding one or more chiral products (e.g., haloalkanes, haloalcohols, alcohols, halopolyols, polyols) by incubating the reagent or reagents with one or more wild type or modified haloalkane dehalogenase. The hydrolytic dehalogenation of the reagent catalysed by the enzyme haloalkane dehalogenase is performed in an aqueous buffer system (e.g., potassium phosphate buffer, Tris-sulfate buffer, glycine buffer, acetate buffer, citrate buffer) at pH being close to the optimum of the haloalkane dehalogenase (pH=7.0-8.5). The pH-activity profile is broader and allows pH variations from 4 to 12 while maintaining a reasonable activity. The variation of pH and buffer type may influence the selectivity of the reaction since the conformation of the enzyme depends on its ionization state. The hydrolytic dehalogenation catalysed by the enzyme can be performed at the temperature range 10-70° C. with reaction optimum around 40° C. The concentration of the enzyme is set with respect to the reaction rate. The concentration of the reagent is dependent on the solubility of the reagent in reaction medium. The methods of the present invention can employ many different halohydrocarbon and haloalkane reagents (e.g., molecules, molecular appendages or substituent groups, etc.) that typically include from about one to about 100 carbon atoms. The carbon atoms or one or more subsets of the carbon atoms can include a straight chain structure, a branched structure, a ring structure, a double bond, a triple bond, and the like. For example, a preferred general class of reactants can include essentially any haloalkane whether cyclic or acyclic (e.g., haloalkanes, haloalkenes, haloalkynes, haloalkyl nitriles, haloalkyl amides, haloalkyl carboxylic acids, haloalkyl carboxylic acid esters, haloalcohols, halopolyols, haloepoxides, haloalkylethers). The reactant can be a xenobiotic or a naturally occurring compound, which can also be a component of a mixture derived from various chemical manufacturing operations or from other processes. Additionally, reaction pathways can involve various intermediates and reactants (e.g., with at least one prochiral or chiral center) that can be enantioselectively or enantiospecifically converted to products.

The hydrolytic dehalogenation of the reagent can be catalysed by the enzyme expressed in the natural producer or in a heterologous host organism, in non-living or living cells, crude extract or purified, immobilized on a carrier material, free in aqueous solution, in a monophasic organic/aqueous solution or in organic/aqueous biphasic systems, under atmospheric or elevated pressure and the like. Organic solvents can be utilized to allow the use of a high reagent concentration, to increase the productivity of the reaction and to favour enzymatic stereoselective reaction over spontaneous hydrolysis. Addition of water-miscible organic co-solvents, e.g., methanol, tert-butanol, acetone, dioxane, acetonitrile, dimethyl formamide, dimethyl sulfoxide, tetrahydrofurane, 3-methyl-3-pentanol and pyridine, can be used at a concentration of up to 70% of the total volume depending on the enzyme stability.

Reaction systems consisting of two macroscopic phases, namely, the aqueous phase containing the dissolved enzyme and the second phase of organic solvents, e.g., ethyl acetate, diethyl ether, methyl tert-butyl ether, cyclohexanol, n-propylacetate, ethyl chloroacetate, bis(2-chloroethyl)ether, isopropyl acetate, butyl acetate, isobutyl acetate, hexanol, isoamyl acetate, n-amyl acetate, toluene, octanol, isoheptane, butyl ether, cyclohexane, 2-methylpentane, n-hexane, methylcyclohexane or n-octane, can be used to achieve a spatial separation of the enzyme from the organic phase. The reaction takes place in aqueous phase where the enzyme is in favourable environment and not in direct contact with the organic solvent, where majority of the substrate and/or product is located. A sufficient mass transfer of the reagent to the enzyme, the product from the enzyme and between the two phases can be obtained by shaking or stirring. The bulk water can be replaced by water immiscible organic solvent and the solid enzyme is then suspended in a monophasic organic solution. Optimum catalytic activity of the enzyme in the organic solvent can be reached by adjustment and maintenance of water-content. This can be conventionally achieved by a pair of salt-hydrates, e.g., $CaCl_2.H_2O/2H_2O$, $NaI$ anh./$2H_2O$, $Na_2HPO_4$ anh./$2H_2O$, $NaOAc$ anh./$3H_2O$, $NaBr$ anh./$2H_2O$, $Na_4P_2O_7$ anh./$7H_2O$, $Na_2HPO_4.2H_2O/7H_2O$, $Na_2SO_4$ anh./$10H_2O$, $Na_2HPO_4.7H_2O/12H_2O$, added to the solvent by functioning as a water-buffer. Alternatively, a saturated salt solution, e.g., $LiBr$, $LiCl$, $MgCl_2$, $K_2CO_3$, $Mg(NO_3)_2$, $NaBr$, $NaCl$, $KCl$, $K_2SO_4$, being in equilibrium with a sufficient amount of undissolved salt, can be circulated through the reaction compartment via a silicone tubing that is submerged in the reaction medium. Any water produced or consumed during the reaction is equilibrated by diffusion through the tube walls, maintaining an equilibrium water activity set by the salt solution.

Surfactants (e.g., Bio-Terge AS-40, Standapol ES-1, Chemal LA-9, Tetronic 1307, Geropon T-77, Rhodasurf ON-870, Trition X45, BRIJ 35, TWEEN, Igepal CA210, Ninate 411, Trition X305, Surfactant 10G, Silwet L7600, BioTerge AS-40, Brij 96, Aerosol OT, or anionactive surfactant of general formula $C_nH_{2n+1}OSO_3Me$, where n ranges from 10 to 16 and Me means opposite ion [$Na^+$, $K^+$ or monoethanolamonium]), can be added to the reaction mixture to achieve a lower surface tension, a better solubility of lipophilic reactants in reaction environment and for the formation of stable emulsions of two or more immiscible liquids. By addition of the surfactant to the reaction mixture, composed from the water phase with soluble protein and the second phase which is the organic solvent, we can get the emulsion wherein the hydrophilic parts of the surfactant molecules are oriented into the small droplets of water phase closing the enzyme and the lipophilic parts of the molecules are oriented to the second phase, to the organic solvent.

The enzyme solubility in lipophilic organic solvents can be modified by covalent attachment of the amphipathic polymer polyethylene glycol (PEG) to the surface of the enzyme. Linkage of the polymer chain onto the enzyme surface is achieved by reaction of ε-amino groups of lysine residues with a 'linker', e.g., cyanuric chloride. Protein stabilizers such as polyalcohols, e.g., sugar alcohols or glycerol, inactive proteins, e.g., bovine serum albumin, or polymers, which have a certain structural resemblance to that of water, e.g., polyethylene glycol, polyvinyl alcohol, can be added to the reaction medium to increase stability of the enzyme.

The physical state of the enzyme may be crystalline, lyophilized or precipitated. The enzymes can be immobilized by adsorption, e.g., inorganic and organic material such as diatomaceous earth (Celite), activated charcoal, aluminium oxide, cellulose, synthetic resins, ionic binding, e.g., cation exchange resins such as carboxymethyl cellulose or Amberlite IRA or anion exchange resins such as N,N-diethyl-aminoethylcellulose or Sephadex, or covalent attachment onto the surface of a macroscopic organic or inorganic carrier material. In general, covalent immobilization involves two steps: (i) activation of the carrier with a reactive 'spacer' group and (ii) enzyme attachment. The functional groups of the enzyme, which are commonly involved in covalent binding, are nucleophilic, e.g., N-terminal and ε-amino groups of lysine or carboxy-, sulfhydryl-, hydroxyl-, and phenolic functions. Inorganic, e.g., porous glass, or organic, e.g., cellulose, dextran, starch, chitin, agarose, carrier and synthetic co-polymers, e.g., VA-Epoxy Biosynth, Eupergit, can be used for covalent immobilization. The enzyme molecules can be immobilized by a cross-linking (linkage to each other) by bifunctional reagent, e.g., glutardialdehyde, dimethyladipimidate, dimethyl suberimidate, hexamethylenediisocyanate.

The enzyme can be confined to a restricted area where it remains catalytically active—entrapment into a solid matrix or membrane-restricted compartments. The enzyme in non-living or living cells can be entrapped into a biological matrix, e.g., agar gel, alginate gel, κ-carragenane. The gel-formation may be initiated by a variation of the temperature or by changing the ionotropic environment of the system. An agar gel is obtained by dropping a mixture of cells in warm (40° C.) solution of agar into well-stirred ice-cold (0-5° C.) aqueous buffer. Calcium-alginate or κ-carragenane gels are prepared by dropping the cell containing sodium alginate solution to a $CaCl_2$- or KCl-solution, respectively.

The enzyme can be entrapped to inorganic stable matrices, e.g., silica gel. The sol-gel process is initiated by the hydrolysis of a tetraalkoxysilane of the type $Si(OR)_4$, where R is a short chain alkyl group, e.g., n-propyl, n-butyl, in the presence of the enzyme. Hydrolysis and condensation of the $Si(OR)_4$ monomers, catalysed by a weak acid or base, triggers the cross-linking and simultaneous formation of amorphous $SiO_2$. A tight network, which is able to carry isolated enzyme, can be obtained by polymerization of synthetic monomers, e.g., polyacrylamide, in the presence of the enzyme. Depending on the immobilization technique, the properties of the enzyme such as stability, selectivity, catalytic rate, binding affinity and temperature characteristics may be significantly altered.

Enzyme can be separated from the rest of the reaction medium by a membrane. Small substrate and/or product molecule can freely diffuse through the membrane, but the large enzyme cannot. Mixture of an aqueous buffer, an organic solvent and a detergent, e.g., Triton, bis(2-ethylhexyl)sodium sulfosuccinate, cetyltrimethyl ammonium bromide, give 'reverse micelles' in arrangement where the organic solvent constitutes the bulk phase. A double layer 'vesicles' (liposomes) can be formed when water is the bulk phase. The aqueous environment entrapped inside these micro-cells contains the enzyme. The enzyme can be detained in a reaction compartment by a synthetic membrane, based on polyamide or polyethersulfone, of defined pore size (1000-10 000 Dalton). A variety of shapes of the synthetic membrane can be used (e.g., foils, hollow fibres). In simple form, the enzyme solution can be enclosed in dialysis tubing, like a tea bag, mounted on a gently rotating magnetic stirring bar.

The substrate specificity, stereo- or regio-selectivity of the hydrolytic dehalogenation catalysed by haloalkane dehalogenase can be improved by an alteration of the enzyme using the rational design based on structural analysis, e.g., protein crystallography, nuclear magnetic resonance and circular dichroism spectroscopy, and biochemical characterization, e.g., steady-state kinetics, transient kinetics, stability and thermostability assays, spectroscopic analyses and the like, followed by computer modelling, e.g., sequence comparisons, phylogenetic analysis, homology modelling, molecular docking, molecular mechanics, molecular dynamics, quantum mechanics and multivariate statistics, and DNA mutagenesis, e.g., cassette mutagenesis, site-directed mutagenesis, chemical mutagenesis, error-prone PCR, site saturation mutagenesis, ensemble mutagenesis, recursive ensemble mutagenesis, scanning saturation mutagenesis, mutator strains, etc. The procedure includes altering at least one amino acid residue of the haloalkane dehalogenases (EC 3.8.1.5) or recombining two or more members of the haloalkane dehalogenases (EC 3.8.1.5) to obtain an enzyme with improved substrate specificity, stereo- or regio-selectivity. Thereafter, the altered haloalkane dehalogenase nucleic acids can be expressed to provide an altered haloalkane dehalogenase. Optionally, the altered haloalkane dehalogenase nucleic acids can be introduced into a cell, in which the introduced altered haloalkane dehalogenase nucleic acids can be expressed to provide an altered haloalkane dehalogenase.

EXAMPLES

Example 1

Preparation of optically pure (S)-2-pentanol by stereoselective hydrolytic dehalogenation of 2-bromopentane catalysed by the haloalkane dehalogenase DbjA (SEQ ID No. 1, 2) isolated from *Bradyrhizobium japonicum* USDA110

Figure 1:
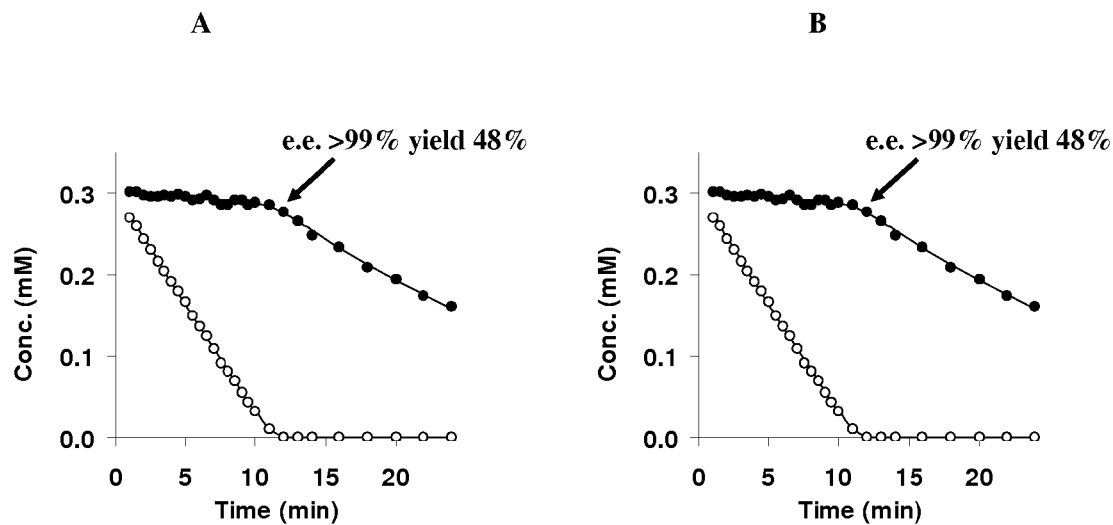
FIG. 1 represents the enantiomeric discrimination of 2-bromopentane by using haloalkane dehalogenase DbjA from *Bradyrhizobium japonicum* USDA110. Racemic 2-bromopentane (A) was converted enantioselectively to 2-pentanol (B). Concentration of both enantiomers (S-enantiomer, black circles) and (R-enantiomer, empty circles) of 2-bromopentane in time.

To overproduce DbjA wild type enzyme, the corresponding gene was cloned in the pYBJA2 vector and transcribed by the tac promoter ($P_{tac}$) under the control of $lacI^q$. *Escherichia coli* BL21 containing the pAQN plasmid was cultured in 0.25 L of Luria broth at 37° C. The induction of the enzyme synthesis was initiated by the addition of isopropyl-β-D-thiogalactopyranoside to a final concentration of 0.5 mM when the culture reached an optical density of 0.6 at 600 nm. After induction, the culture was incubated at 30° C. for 4 h and then harvested. The cells were disrupted by sonication using Soniprep 150 (Sanyo, UK). The supernatant was used after centrifugation at 100,000×g for 1 h. The dehalogenase was purified on a Ni-NTA Sepharose column HR 16/10 (Qiagen, Germany). The His-tagged DbjA was bound to the resin in the equilibrating buffer, which contained 20 mM potassium phosphate buffer pH 7.5, 0.5 M sodium chloride and 10 mM imidazole. Unbound and weakly bound proteins were washed off by buffer containing 60 mM imidazole. The His-tagged DbjA enzyme was then eluted by buffer with 160 mM imidazole. The active fractions were pooled and dialysed overnight against 50 mM potassium phosphate buffer, pH 7.5. The enzyme was stored at 4° C. in 50 mM potassium phosphate buffer, pH 7.5, containing 10% glycerol and 1 mM 2-mercaptoethanol. The hydrolytic dehalogenation of racemic 2-bromopentane was catalysed by haloalkane dehalogenase DbjA at a room temperature (21° C.) in 20 ml of buffer containing 50 mM tris(hydroxymethyl)aminomethane (pH 8.2, adjusted by addition of $H_2SO_4$). The reaction was initiated by addition of purified haloalkane dehalogenase DbjA to a final enzyme concentration 1 μM. The method uses a high magnitude of chiral recognition of 2-bromopentane by the haloalkane dehalogenase DbjA (E-value>145). The reaction was stopped after the complete conversion of the preferred enantiomer. Optically pure (S)-2-bromopentane with enantiomeric excess of 99% and yield 48% and optically pure (S)-2-pentanol with enantiomeric excess of 96% and yield 48% were obtained (FIG. 1).

Example 2

Preparation of Optically Pure Methyl (S)-Lactate by Stereoselective Hydrolytic dehalogenation of methyl 2-bromopropionate catalysed by the haloalkane dehalogenase DhaA (SEQ ID No. 5, 6) isolated from *Rhodococcus rhodochrous* NCIMB 13064.

Figure 2:
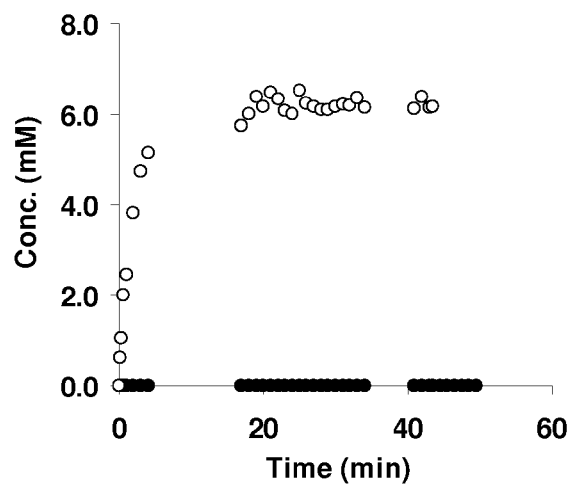
FIG. 2 represents the time course of the synthesis of optically pure methyl (S)-lactate by stereoselective hydrolytic dehalogenation of methyl 2-bromopropionate catalysed by haloalkane dehalogenase DhaA isolated from *Rhodococcus rhodochrous*. Concentration of methyl (S)-lactate (empty circles) and methyl (R)-lactate (black circles) in time.

To overproduce DhaA wild type enzyme, the corresponding gene was cloned in the pAQN vector and transcribed by the tac promoter ($P_{tac}$) under the control of $lacI^q$. *Escherichia coli* BL21 containing the pAQN plasmid was cultured in 0.25 L of Luria broth at 37° C. The isopropyl-β-D-thiogalactopyranoside to a final concentration of 0.5 mM was added when the culture reached an optical density of 0.6 at 600 nm. The culture was incubated at 30° C. for 4 h and then harvested. The cells were disrupted by sonication using Soniprep 150 (Sanyo, UK). The supernatant was used after centrifugation at 100,000×g for 1 h. The His-tagged DhaA was purified on a Ni-NTA Sepharose column HR 16/10 (Qiagen, Germany). The enzyme was stored at 4° C. in 50 mM potassium phosphate buffer, pH 7.5, containing 10% glycerol and 1 mM 2-mercaptoethanol. Hydrolytic dehalogenation of racemic ethyl 2-bromobutyrate was catalysed by DhaA enzyme at room temperature (21° C.) in 1 L batch stirred reactor in 50 mM Tris(hydroxymethyl)aminomethane (pH=8.2; by $H_2SO_4$). The reaction was initiated by addition of purified haloalkane dehalogenase DhaA to final enzyme concentration 5 μM. The method uses a high magnitude of the chiral recognition of methyl 2-bromopropionate by the haloalkane dehalogenase DhaA (E-value >200). After complete conversion of the preferred enantiomer, high enantiomeric purity of methyl (S)-lactate was reached (e.e.>99.9%). The optically pure methyl (S)-lactate can be easily separated from the reaction mixture (FIG. 2).

Example 3

Preparation of optically pure ethyl (S)-2-hydroxybutyrate by stereoselective hydrolytic dehalogenation of ethyl 2-brombutyrate catalysed by the haloalkane dehalogenases DbjA, LinB, DhaA, DmbA, DmbB, DmbC, DrbA, DhmA and DbeA The wild type enzymes DbjA, LinB, DhaA, DmbA, DmbB, DmbC, DrbA, DhmA and DbeA were prepared by overproduction in *Escherichia coli* BL21. Every corresponding gene was cloned in the pAQN vector and transcribed by the tac promoter ($P_{tac}$) under the control of lacI$^q$. *Escherichia coli* BL21 containing the pAQN plasmid was cultured in 0.25 L of Luria broth at 37° C. The isopropyl-β-D-thiogalactopyranoside was added to a final concentration of 0.5 mM when the culture reached the optical density of 0.6 at 600 nm. The culture was incubated at 30° C. for 4 h and then harvested. The cells were disrupted by sonication using Soniprep 150 (Sanyo, UK). The supernatant was used after centrifugation at 100,000×g for 1 h. His-tagged haloalkane dehalogenases were purified on a Ni-NTA Sepharose column HR 16/10 (Qiagen, Germany). The enzyme was stored at 4° C. in 50 mM potassium phosphate buffer, pH 7.5, containing 10% glycerol and 1 mM 2-mercaptoethanol. Chiral recognition of ethyl 2-bromobutyrate was tested with the following haloalkane dehalogenases: DbjA, LinB, DhaA, DmbA, DmbB, DmbC, DrbA, DhmA and DbeA. The reactions were performed at room temperature (21° C.) in 20 ml of reaction mixture containing 50 mM Tris(hydroxymethyl)aminomethane (pH=8.2; by $H_2SO_4$). The reactions were initiated by the addition of purified haloalkane dehalogenases to the final enzyme concentration of 1 μM. The method uses a high magnitude of the chiral recognition of ethyl 2-bromobutyrate by haloalkane dehalogenases (Table 2). In all cases, the conversion of ethyl 2-bromobutyrate by the haloalkane dehalogenases DbjA, LinB, DhaA, DmbA, DmbB, DmbC, DrbA, DhmA and DbeA, respectively, proceeds to the entire conversion of the preferred enantiomer and 99.9% enantiomeric excess of ethyl (S)-2-hydroxybutyrate is reached.

TABLE 2

Chiral recognition of ethyl 2-bromobutyrate by hydrolytic dehalogenation catalysed by the haloalkane dehalogenases DbjA, LinB, DhaA, DmbA, DmbB, DmbC, DrbA, DhmA and DbeA.

| Substrate | E-values | | | | | | | | |
| --- | --- | --- | --- | --- | --- | --- | --- | --- | --- |
| | DbjA | LinB | DhaA | DmbA | DmbB | DmbC | DrbA | DhmA | DbeA |
| ethyl-2-bromo-butyrate | >200 | >200 | >200 | >200 | >200 | >200 | >200 | >200 | >200 |

Example 4

Preparation of optically pure ethyl (S)-2-bromopropionate and ethyl (S)-lactate by stereoselective hydrolytic dehalogenation of racemic ethyl 2-bromopropionate catalysed by modified protein MUT01 (SEQ ID No. 19, 20) with haloalkane dehalogenase activity Modified protein MUT01 with haloalkane dehalogenase activity having an amino acid sequence showing between 21.1 and 93.7% identity with amino acid sequences of haloalkane dehalogenases DbjA, LinB, DhaA, DmbA, DmbB, DmbC, DrbA, DhmA and DbeA (Table 3) was used for preparation of optically pure (S)-2-hexanol and (S)-ethyl lactate. Modified protein MUT01 is coded by the gene with DNA sequence showing between 32.4 and 94.8% identity to DNA sequences of DbjA, LinB, DhaA, DmbA, DmbB, DmbC, DrbA DhmA and DbeA (Table 3).

TABLE 3

Sequence identity of modified protein MUT01 (SEQ ID No. 19, 20) to sequences of haloalkane dehalogenases DbjA, LinB, DhaA, DmbA, DmbB, DmbC, DrbA, DhmA and DbeA.

| Haloalkane dehalogenase | DNA sequence identity: haloalkane dehalogenases vs. MUT01 (SEQ ID No. 19) | Amino acid sequence identity: haloalkane dehalogenases vs. MUT01 (SEQ ID No. 20) |
| --- | --- | --- |
| DbjA | 58.3% | 52.5% |
| LinB | 51.7% | 46.9% |
| DhaA | 94.8% | 93.7% |
| DmbA | 51.4% | 42.4% |
| DmbB | 38.7% | 26.5% |
| DmbC | 37.5% | 24.6% |
| DrbA | 32.4% | 21.1% |
| DhmA | 39.7% | 26.4% |
| DbeA | 54.7% | 47.9% |

Figure 3:
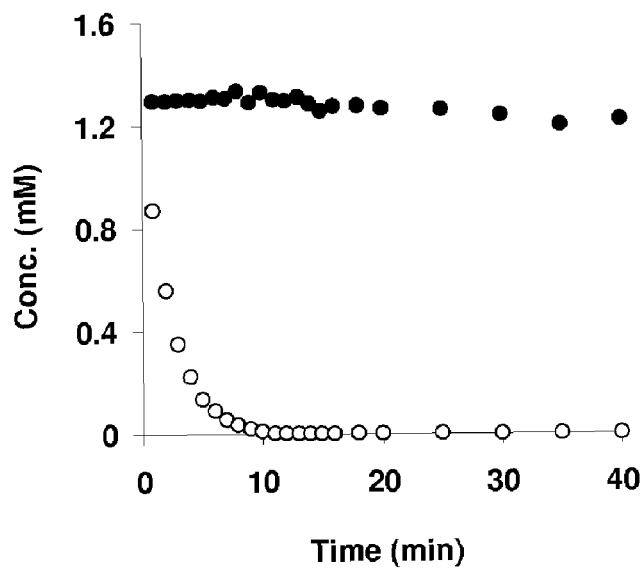
FIG. 3 represents the enantiomeric discrimination of ethyl 2-bromopropionate by modified protein MUT01 with haloalkane dehalogenase activity. Concentration of ethyl (R)-2-bromopropionate (empty circles) and ethyl (S)-2-bromopropionate (black circles) in time.

Recombinant gene of the modified protein was obtained by using QuikChange™ Site-Directed Mutagenesis Kit (Stratagene, USA). Plasmid pUC19 with recombinant gene was used as the first template. Mutant recombinant gene was recloned into pET21b vector. Resulting plasmid containing the recombinant gene MUT01 was transformed to host organism *E. coli* BL21 (DE3). The host organism *E. coli* BL21 (DE3) was cultivated in 250 ml Luria broth at 37° C. Isopropyl-β-D-thiogalactopyranoside was added to final concentration of 0.5 mM when the culture reached an optical density of 0.6 at 600 nm. The culture was incubated at 30° C. for 4 h and then harvested. The cells were disrupted by sonication using Soniprep 150 (Sanyo, UK). The supernatant was used after centrifugation at 100,000×g for 1 h. The modified protein MUT01 with his-tag was purified on a Ni-NTA Sepharose column HR 16/10 (Qiagen, Germany). The enzyme was stored at 4° C. in 50 mM potassium phosphate buffer, pH 7.5, containing 10% glycerol and 1 mM 2-mercaptoethanol. The hydrolytic dehalogenation of racemic 2-bromohexane and racemic ethyl 2-bromopropionate was catalysed by modified protein MUT01 at a room temperature (21° C.) in 20 ml of buffer containing 50 mM tris(hydroxymethyl)aminomethane (pH 8.2, adjusted by addition of $H_2SO_4$). The reaction was initiated by addition of purified protein MUT0 to a final concentration 1 µM. The method uses high magnitude of the chiral recognition of ethyl 2-bromopropionate (E-value>200) by protein MUT01 with haloalkane dehalogenase activity. After entire conversion of preferred enantiomer of ethyl 2-bromopropionate with high enantiomer excess is reached and the resulting optically pure ethyl (S)-lactate with e.e. 99.9% and optically pure ethyl (S)-2-bromopropionate (e.e. =99.9%) can be easily separated (FIG. 3).

Example 5

Preparation of optically pure 2-bromopropiophenone by stereoselective hydrolytic dehalogenation of racemic mixture by the haloalkane dehalogenase DbjA (SEQ ID No. 1, 2) from *Bradyrhizobium japonicum* and DhaA (SEQ ID No. 5, 6) from *Rhodococcus rhodochrous*

Figure 4:
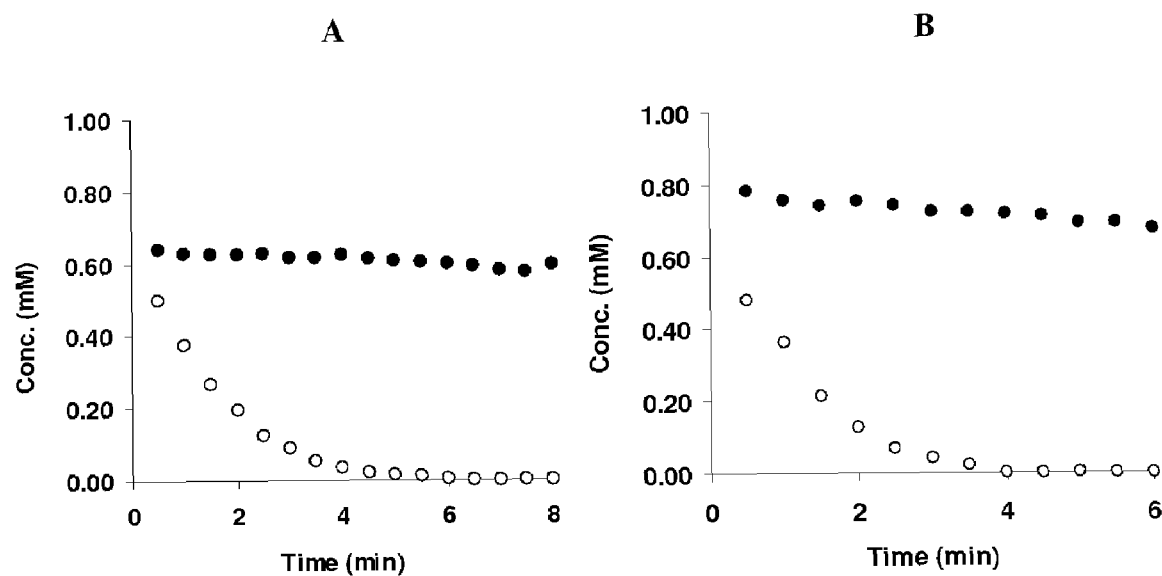
FIG. 4 represents the enantiomeric discrimination of 2-bromopropiophenone by the haloalkane dehalogenases DhaA (A) and DbjA (B). Concentration of both enantiomers (black and empty circles) of methyl lactate in time.

To overproduce DbjA and DhaA wild type enzymes, the corresponding genes were cloned in the pYBJA2 vector and transcribed by the tac promoter ($P_{tac}$) under the control of lacI$^q$. *Escherichia coli* BL21 containing the pAQN plasmid was cultured in 0.25 L of Luria broth at 37° C. The induction of the enzyme synthesis was initiated by the addition of isopropyl-β-D-thiogalactopyranoside to a final concentration of 0.5 mM when the culture reached an optical density of 0.6 at 600 nm. After induction, the culture was incubated at 30° C. for 4 h and then harvested. The cells were disrupted by sonication using Soniprep 150 (Sanyo, UK). The supernatant was used after centrifugation at 100,000×g for 1 h. The dehalogenase was purified on a Ni-NTA Sepharose column HR 16/10 (Qiagen, Germany). The His-tagged DbjA was bound to the resin in the equilibrating buffer, which contained 20 mM potassium phosphate buffer pH 7.5, 0.5 M sodium chloride and 10 mM imidazole. Unbound and weakly bound proteins were washed off by buffer containing 60 mM imidazole. The His-tagged DbjA enzyme was then eluted by buffer with 160 mM imidazole. The active fractions were pooled and dialysed overnight against 50 mM potassium phosphate buffer, pH 7.5. The enzyme was stored at 4° C. in 50 mM potassium phosphate buffer, pH 7.5, containing 10% glycerol and 1 mM 2-mercaptoethanol. The hydrolytic dehalogenation of racemic 2-bromopropiophenone was catalysed by the haloalkane dehalogenases DbjA and DhaA, respectively, at a room temperature (21° C.) in 20 ml of buffer containing 50 mM tris (hydroxymethyl)aminomethane (pH 8.2, adjusted by addition of $H_2SO_4$). The reaction was initiated by addition of the purified haloalkane dehalogenase DbjA or DhaA to a final enzyme concentration 1 µM. The method uses a high magnitude of the chiral recognition of 2-bromopropiophenone by the haloalkane dehalogenase DbjA (E-value>200). The reaction was stopped after complete conversion of preferred enantiomer. Final enantiomeric excess>99.5% was reached for optically pure non-preferred enantiomer of 2-bromopropiophenone in reactions catalysed by both DbjA and DhaA (FIG. 4).

Example 6

Rational Engineering of Specificity of the Haloalkane Dehalogenase LinB (SEQ ID No. 3, 4) Using Phylogenetic Analysis and Computer Modelling The amino acid Leucine (Leu) in position 177 was identified as a determinant of the substrate specificity of haloalkane dehalogenase LinB by structural analysis and comparison of the primary sequence of LinB (SEQ ID NO: 4) with protein sequences of other haloalkane dehalogenase family members. Leu 177 is positioned at the mouth of the largest entrance tunnel leading to the enzyme active site and is pointing directly into the tunnel. At the same time it is the most variable pocket residue of the haloalkane dehalogenase-like proteins showing 9 different substitutions in 14 proteins. Saturated mutagenesis in position 177 of LinB was performed using site-directed mutagenesis. The plasmid pULBH6 was used as a template. To overproduce LinB mutants in *E. coli*, His-tagged mutant LinB genes were cloned in pAQN vector and the genes were transcribed by the tac promoter (P tac) under the control of lacI$^q$. *E. coli* BL21 containing these plasmids were cultured in 1 L of Luria broth. When the culture reached an optical density of 0.6 at 600 nm the induction of enzyme expression (at 30° C.) was initiated by the addition of isopropyl-β-D-thiogalactopyranoside to a final concentration of 1 mM. The cells were harvested and disrupted by sonication using a Soniprep 150 (Sanyo Gallenkamp PLC, Loughborough, UK). The supernatant was used after centrifugation at 100,000×g for 1 hr. The crude extract was further purified on a Ni-NTA Sepharose column HR 16/10 (QIAGEN, Hilden, Germany). The His-tagged LinB mutants were bound to the resin in the equilibrating 20 mM potassium phosphate buffer (pH 7.5) containing 0.5 M sodium chloride and 10 mM imidazole. Unbound and weakly bound proteins were washed out by the buffer containing 45 mM imidazole. The His-tagged enzyme was then eluted by the buffer containing 160 mM imidazole. The active fractions were pooled and dialysed against 50 mM potassium phosphate buffer (pH 7.5) overnight. The enzyme was stored in 50 mM potassium phosphate buffer (pH 7.5) containing 10% glycerol and 1 mM 2-mercaptoethanol. Specific activities of LinB with twelve different halogenated substrates representing different chemical groups (mono-, di- and tri-halogenated, chlorinated, brominated and iodinated; α- and β-substituted, aliphatic and cyclic, saturated and unsaturated compounds) were assessed (Table 4).

TABLE 4

Substrate specificity of purified wild type and mutant haloalkane dehalogenases.

| Proteins | Relative activities (% of wt) | | | | | | | | | |
|---|---|---|---|---|---|---|---|---|---|---|
| | wt1[a] | L177A | L177C | L177G | L177F | L177K | L177T | L177W | wt2[b] | L177D |
| 1-chlorobutane | 100 | 142 | 37 | 94 | 229 | 61 | —[c] | 138 | 100 | 104 |
| 1-chlorohexane | 100 | 106 | 179 | 125 | 215 | 100 | 143 | 89 | 100 | 44 |
| 1-bromobutane | 100 | 356 | 243 | 380 | 243 | 201 | 553 | 60 | 100 | 347 |
| 1-iodobutane | 100 | 133 | 210 | 344 | 126 | 131 | 424 | 58 | 100 | 259 |
| 1,2-dichloroethane | —[c] | —[c] | —[c] | —[c] | —[c] | —[c] | —[c] | —[c] | —[c] | —[c] |
| 1,2-dibromoethane | 100 | 155 | 52 | 78 | 70 | 97 | 107 | 7 | 100 | 77 |
| 1,3-diidopropane | 100 | 360 | 192 | 164 | 130 | 132 | 108 | 117 | 100 | 209 |
| 1,2-dichloropropane | —[c] | —[c] | —[c] | —[c] | —[c] | —[c] | —[c] | —[c] | —[c] | —[c] |
| 1,2,3-trichloropropane | —[c] | —[c] | —[c] | —[c] | —[c] | —[c] | —[c] | —[c] | —[c] | —[c] |
| chlorocyclohexane | 100 | —[c] | —[c] | 33 | —[c] | —[c] | —[c] | 139 | 100 | 38 |
| bromocyclohexane | 100 | 115 | 298 | 398 | 267 | 117 | 198 | 80 | 100 | 63 |
| 3-chloro-2-methylpropene | 100 | 199 | 157 | 200 | 98 | 110 | 96 | 91 | 100 | 25 |

| Proteins | Relative activities (% of wt) | | | | | | | | |
|---|---|---|---|---|---|---|---|---|---|
| | L177H | L177I | L177M | L177P | L177Q | L177R | L177S | L177V | L177Y |
| 1-chlorobutane | 56 | —[c] | 144 | —[c] | 54 | 46 | 60 | 74 | 55 |
| 1-chlorohexane | 75 | —[c] | 162 | —[c] | 165 | 31 | 104 | 80 | 80 |
| 1-bromobutane | 224 | —[c] | 227 | —[c] | 458 | 165 | 381 | 132 | 112 |
| 1-iodobutane | 208 | —[c] | 187 | —[c] | 373 | 161 | 363 | 101 | 97 |
| 1,2-dichloroethane | —[c] | —[c] | —[c] | —[c] | —[c] | —[c] | —[c] | —[c] | —[c] |
| 1,2-dibromoethane | 55 | —[c] | 126 | —[c] | 123 | 68 | 84 | 84 | 16 |
| 1,3-diidopropane | 140 | —[c] | 202 | —[c] | 159 | 127 | 123 | 206 | 102 |
| 1,2-dichloropropane | —[c] | —[c] | —[c] | —[c] | —[c] | —[c] | —[c] | —[c] | —[c] |
| 1,2,3-trichloropropane | —[c] | —[c] | —[c] | —[c] | —[c] | —[c] | —[c] | —[c] | —[c] |
| chlorocyclohexane | —[c] | —[c] | 79 | —[c] | —[c] | —[c] | 21 | 91 | — |
| bromocyclohexane | 43 | —[c] | 104 | —[c] | 120 | 37 | 156 | 41 | 41 |
| 3-chloro-2-methylpropene | 82 | —[c] | 100 | —[c] | 138 | 83 | 65 | 79 | 78 |

[a] specific activities (in $\mu mol \cdot s^{-1} \cdot mg^{-1}$ of enzyme) of the wild type enzyme in the first set of mutants are 0.0338 (1-chlorobutane), 0.0208 (1-chlorohexane), 0.0633 (1-bromobutane), 0.0104 (1-iodobutane), 0.2200 (1,2-dibromoethane), 0.0463 (1,3-diidopropane), 0.0018 (chlorocyclohexane), 0.0201 (bromocyclohexane) and 0.1366 (3-chloro-2-methylpropene).
[b] specific activities (in $\mu mol \cdot s^{-1} \cdot mg^{-1}$ of enzyme) of the wild type enzyme in the second set of mutants are 0.0287 (1-chlorobutane), 0.0315 (1-chlorohexane), 0.0477 (1-bromobutane), 0.0408 (1-iodobutane), 0.1894 (1,2-dibromoethane), 0.0262 (1,3-diidopropane), 0.0034 (chlorocyclohexane), 0.0336 (bromocyclohexane) and 0.1312 (3-chloro-2-methylpropene).
[c] activity not detectable Without exception, all mutants exhibited modified activities compared to the wild type enzyme. In general, activity of LinB enzyme increases with the introduction of small and non-polar amino acid to the position 177. This residue is partially blocking the entrance tunnel and its size and polarity influence binding of the substrate molecules to the active site. Especially poor binding is observed when negative charge is introduced in position 177 ($K_m$ for mutant where Leu 177 was substituted by Asp is 21.9 mM with 1-chlorobutane and 14 mM with 1,2-dibromoethane). The activity and substrate specificity of haloalkane dehalogenase can obviously be modulated by the residues positioned far from the active site if they are a part of the entrance tunnel. Modification of the catalytic properties of haloalkane dehalogenases using site-directed mutagenesis by specifically targeting such distant residues (identified using rational design) provides functional enzymes at much higher rate compared to mutagenesis of the active site residues.

Example 7

Hydrolytic dehalogenation of 1-iodohexane catalysed by haloalkane dehalogenase DbjA (SEQ ID No. 1, 2) isolated from *Bradyrhizobium japonicum* USDA110 in the presence of organic solvents Hydrolytic dehalogenation of 1-iodohexane catalysed by haloalkane dehalogenase DbjA isolated from *Bradyrhizobium japonicum* USDA110 was performed in presence of organic solvents. Reaction mixture was prepared by mixing glycine buffer (7.5 g glycine in 1 L distilled water, pH was adjusted to value 8.6 by addition of NaOH solution) with appropriate volumes of organic solvents to reach specified final concentrations (5, 10, 20% v/v; volume concentration of organic solvent in water buffer). The substrate 1-iodohexane was added to the reaction mixture to final concentration 1 mM. The reaction was initiated by addition of enzyme DbjA to a final enzyme concentration 1 μM. The reaction was monitored by colorimetric detection of iodide ion concentration increase by using Iwasaki method [Iwasaki, I., Utsumi, S., Ozawa, T. *Bulletin of the Chemical Society of Japan* (1952) 25, 226].

The enzyme DbjA has shown high tolerance to the presence of all the tested organic solvents in concentration 5 and 10% (v/v). The DbjA enzyme has shown an increasing activity in the presence of acetone, 1,4-dioxane and methanol in the reaction medium. The hydrolytic dehalogenation of 1-iodohexane catalysed by haloalkane dehalogenase DbjA reached 1.68 times increase of reaction rate in the 20% (v/v) acetone compared to that in the glycine buffer.

Haloalkane dehalogenases can catalyse hydrolytic dehalogenation not only in aqueous solution but also in the environment of organic solvents, where the higher solubility of desired substrate and higher reaction rate of enzyme are achieved at the same time.

The undesired side reactions are suppressed and enantioselectivity can be improved in the presence of organic solvents as well.

and then harvested. The cells were disrupted by sonication using Soniprep 150 (Sanyo, UK). The supernatant was used after centrifugation at 100,000×g for 1 h. The dehalogenase was purified on a Ni-NTA Sepharose column HR 16/10 (Qiagen, Germany). The His-tagged DbeA was bound to the resin in the equilibrating buffer, which contained 20 mM potassium phosphate buffer pH 7.5, 0.5 M sodium chloride and 10 mM imidazole. Unbound and weakly bound proteins were washed off by buffer containing 60 mM imidazole. The His-tagged DbeA enzyme was then eluted by buffer with 160 mM imidazole. The active fractions were pooled and dialysed overnight against 50 mM potassium phosphate buffer, pH 7.5. The enzyme was stored at 4° C. in 50 mM potassium phosphate buffer, pH 7.5, containing 10% glycerol and 1 mM 2-mercaptoethanol. The hydrolytic dehalogenation of racemic 2-bromopentane was catalysed by haloalkane dehalogenase DbeA at a room temperature (21° C.) in 20 ml of buffer containing 50 mM tris(hydroxymethyl)aminomethane (pH 8.2, adjusted by addition of $H_2SO_4$). The reaction was initiated by addition of purified haloalkane dehalogenase DbeA to a final enzyme concentration 1 μM. The method uses a high magnitude of chiral recognition of 2-bromopentane by the

TABLE 5

Relative activities of DbjA in the presence of organic solvents.

| | | Relative enzyme activity (%) | | |
|---|---|---|---|---|
| Organic solvent | log P (a) | 5% (b) of solvent | 10% (b) of solvent | 20% (b) of solvent |
| glycine buffer | — | | 100.0 ± 6.8 (c) | |
| Formamide | -1.57 | 73.4 ± 7.6 | 76.3 ± 5.0 | 16.3 ± 0.6 |
| Formamide | -1.57 | 73.4 ± 7.6 | 76.3 ± 5.0 | 16.3 ± 0.6 |
| ethyleneglycol | -1.23 | 87.1 ± 9.8 | 80.5 ± 8.9 | 109.8 ± 4.0 |
| N,N-dimethylformamide | -1.04 | 110.5 ± 11.6 | 112.6 ± 3.8 | 101.9 ± 1.0 |
| Methanol | -0.82 | 93.5 ± 0.9 | 128.7 ± 3.5 | 160.7 ± 2.0 |
| 1,4-dioxane | -0.50 | 121.4 ± 3.9 | 139.9 ± 7.8 | 152.0 ± 9.5 |
| acetonitrile | -0.39 | 117.5 ± 8.9 | 124.1 ± 1.0 | 0.0 ± 0.0 |
| ethanol | -0.32 | 106.8 ± 8.9 | 91.8 ± 7.3 | 102.2 ± 2.2 |
| acetone | -0.24 | 113.8 ± 7.3 | 140.3 ± 2.1 | 168.2 ± 3.1 |
| tetrahydrofurane | 0.46 | 111.9 ± 13.4 | 96.9 ± 9.0 | 0.0 ± 0.0 |

(a) logarithm of n-octanol-water partition coefficient
(b) volume concentration of organic solvent in water buffer; (v/v)
(c) relative activity in glycine buffer Example 8

Preparation of optically pure (S)-2-pentanol by stereoselective hydrolytic dehalogenation of 2-bromopentane catalysed by the haloalkane dehalogenase DbeA (SEQ ID No. 17, 18) isolated from *Bradyrhizobium elkanii*

To overproduce DbeA wild type enzyme, the corresponding gene was cloned in the pYBJA2 vector and transcribed by the tac promoter ($P_{tac}$) under the control of lacI$^q$. *Escherichia coli* BL21 containing the pAQN plasmid was cultured in 0.25 L of Luria broth at 37° C. The induction of the enzyme synthesis was initiated by the addition of isopropyl-β-D-thiogalactopyranoside to a final concentration of 0.5 mM when the culture reached an optical density of 0.6 at 600 nm. After induction, the culture was incubated at 30° C. for 4 h haloalkane dehalogenase DbeA (E-value=98). The reaction was stopped after the complete conversion of the preferred enantiomer. Optically pure (S)-2-bromopentane with enantiomeric excess of 97% and yield 47% and optically pure (S)-2-pentanol with enantiomeric excess of 94% and yield 47% were obtained.

INDUSTRIAL APPLICABILITY

The invention can be applied for industrial production of optically active compounds, particularly haloalkanes, haloalcohols, alcohols, halopolyols, polyols, hydroxyketones and hydroxyesters using hydrolytic dehalogenation of racemic or prochiral halogenhydrocarbons by dehalogenation catalysed by haloalkane dehalogenases (EC 3.8.1.5).

The invention claimed is:

1. A method of production of optically active halohydrocarbons and alcohols using hydrolytic dehalogenation catalysed by a haloalkane dehalogenase wherein haloalkane dehalogenase DbjA having the amino acid sequence SEQ ID NO: 2 is applied to at least one racemic or prochiral chlorinated, brominated or iodinated compound at a temperature range between +10 and +70° C. and pH value between 4.0 and 12.0, in an aqueous system or in a monophasic organic solution or in a monophasic organic/aqueous solution or in organic/aqueous biphasic systems, wherein the chlorinated, brominated or iodinated compounds have at least one halogen atom bound directly to the chiral or prochiral carbon and the nucleophilic attack takes place directly on the chiral or prochiral carbon.

2. The method according to claim 1, wherein it is performed in the presence of surfactants to allow using of enhanced reagent concentration.

3. The method according to claim 1, wherein the haloalkane dehalogenase DbjA is in soluble or crystalline or lyophilized or precipitated form.

4. The method according to claim 1, wherein the haloalkane dehalogenase DbjA is immobilized by adsorption or ionic binding or covalent attachment onto the surface of a macroscopic carrier material.

5. The method according to claim 1, wherein the haloalkane dehalogenase DbjA is immobilized by cross-linking or confined to a solid matrix or membrane-restricted compartments.

* * * * *